US007893232B2

(12) United States Patent
Nakao et al.

(10) Patent No.: US 7,893,232 B2
(45) Date of Patent: Feb. 22, 2011

(54) LIPASE

(75) Inventors: Masahiro Nakao, Osaka (JP); Masaki Kanamori, Osaka (JP); Harukazu Fukami, Osaka (JP); Hiroaki Kasai, Kamaishi (JP); Misa Ochiai, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 198 days.

(21) Appl. No.: 12/096,574

(22) PCT Filed: Dec. 8, 2006

(86) PCT No.: PCT/JP2006/324598

§ 371 (c)(1), (2), (4) Date: Jun. 6, 2008

(87) PCT Pub. No.: WO2007/066779

PCT Pub. Date: Jun. 14, 2007

(65) Prior Publication Data

US 2010/0075380 A1 Mar. 25, 2010

(30) Foreign Application Priority Data

Dec. 9, 2005 (JP) ............................ 2005-356936

(51) Int. Cl.
*C07H 21/02* (2006.01)
*C12N 1/20* (2006.01)
*C12N 15/00* (2006.01)

(52) U.S. Cl. ................. 536/23.1; 435/252.3; 435/320.1

(58) Field of Classification Search ....................... None
See application file for complete search history.

(56) References Cited

U.S. PATENT DOCUMENTS 5,290,694 A * 3/1994 Nakanishi et al. ........... 435/198

FOREIGN PATENT DOCUMENTS

| | | | |
|---|---|---|---|
| JP | 5-304949 | | 11/1993 |
| JP | 2002-159290 | | 6/2002 |
| WO | WO 01/16303 | A2 | 8/2001 |
| WO | WO 2004/064537 | A2 | 8/2004 |
| WO | WO 2004/064987 | A2 | 8/2004 |

OTHER PUBLICATIONS

Casimir C. Akoh et al., "GDSL Family of Serine Esterases/Lipases", Progress in Lipid Research, 2004, pp. 534-552, vol. 43, published by Elsevier Ltd.

Dusica Vujaklija et al., "A Novel Streptomycete Lipase: Cloning, Sequencing and High-Level Expression of the *Streptomyces rimosus* GDS (L)—Lipase Gene", Arch. Microbiol., 2002, pp. 124-130, vol. 178, No. 2.

International Search Report mailed Feb. 27, 2007 in International Application No. PCT/JP2006/324598 filed Dec. 8, 2006.

European Search Report issued Dec. 11, 2008, in European patent application No. 08015135.0.

Database UniProt [Online], Accession No. Q4JXK5, Aug. 2, 2005, "Putative secreted protein from *Corynebacterium jeikeium*," XP002505918.

Kawaguchi et al., "The codon CUG is read as serine in an asporogenic yeast *Candida cylindracea*," Nature, vol. 341, Sep. 14, 1989, pp. 164-166, Nature Publishing Group, London, England.

Haas et al., "Cloning, expression and characterization of a cDNA encoding a lipase from *Rhizopus delemar*," Gene, vol. 109, 1991, pp. 107-113, Elsevier, Amsterdam, Holland.

Dartois et al., "Cloning, nucleotide sequence and expression in *Escherichia coli* of a lipase gene from *Bacillus subtilis* 168," Biochemica et Biophysica Acta, vol. 1131, 1992, pp. 253-260.

Ikeda et al., "Lymphatic Absorption of Structured Glycerolipids Containing Medium-Chain Fatty Acids and Linoleic Acid, and Their Effect on Cholesterol Absorption in Rats," Lipids, vol. 26, No. 5, 1991, pp. 369-373.

Lee et al., "Mechanism of Bacteriophage Conversion of Lipase Activity in *Staphylococcus aureus*," Journal of Bacteriology, vol. 164, No. 1, Oct. 1985, pp. 288-293.

Wohlfarth et al., "Molecular genetics of the extracellular lipase of *Pseudomonas aeruginosa*," Journal of General Microbiology, vol. 138, 1992, pp. 1325-1335, Reading Society for General Microbiology, Reading, England.

European Search Report dated May 25, 2009, for European Application No. EP 06 83 4353.

Akoh et al., "GDSL family of serine esterases/lipases," Progress in Lipid Research 43, (2004) pp. 534-552.

* cited by examiner

*Primary Examiner*—Mark Navarro
(74) *Attorney, Agent, or Firm*—Drinker Biddle & Reath LLP

(57) ABSTRACT

The present invention provides a novel lipase with a molecular weight of about 32 kDa, which is produced by a strain belonging to the genus *Tetrasphaera*, as well as a gene encoding the same. This lipase has the ability to recognize a medium-chain fatty acid as a substrate. The present invention also provides a novel lipase with a molecular weight of about 40 kDa, which is produced by a strain belonging to the genus *Tetrasphaera* and has the ability to recognize both a medium-chain fatty acid and a long-chain fatty acid as substrates, as well as a polynucleotide encoding the same. The present invention further provides *Tetrasphaera* sp. strain NITE P-154. The lipase of the present invention can be used as an immobilized enzyme and is useful in fields such as production of digestants and/or flavorings, production of clinical laboratory reagents, detergent enzymes and/or fats, as well as production of optically active intermediates for agricultural chemicals and pharmaceutical preparations.

9 Claims, 12 Drawing Sheets

Figure 1

TAACACATGCAAGTCGAACGGTGACCTCGAGAGCTTGCTCTCGAGCGATCAGTGGCGAACGGGTGAGTAACACGTGAGTAACCTGCCCCAGACTCTGGAATAACCCCGGGA
AACCGGAGCTAATACCGGATACGAGACGAAGCTGCATGGCTATCGTCTGGAAAGTTTTTCGGTCTGGGATGGACTCGCGGCCTATCAGCTTGTTGGTGAGGTAACGGCTCA
CCAAGGCGACGACGGGTAGCCGGCCTGAGAGGGCGACCGGCCACACTGGGACTGAGACACGGCCCAGACTCCTACGGGAGGCAGCAGTGGGGAATATTGCACAATGGGCGC
AAGCCTGATGCAGCGACGCCGCGTGAGGGATGACGGCCTTCGGGTTGTAAACCTCTTTCAGCAGGGAAGAAGCGAAAGTGACGGTACCTGCAGAAGAAGCACCGGCTAACT
ACGTGCCAGCAGCCGCGGTAATACGTAGGGTGCGAGCGTTGTCCGGAATTATTGGGCGTAAAGAGCTTGTAGGCGGTTTGTCGCGTCTGCTGTGAAAATCCGGGGCTCAAC
CCCGGACTTGCAGTGGGTACGGGCAGACTAGAGTGTGGTAGGGGAGACTGGAATTCCTGGTGTAGCGGTGAAATGCGCAGATATCAGGAGGAACACCGATGGCGAAGGCAG
GTCTCTGGGCCACTACTGACGCTGAGAAGCGAAAGCATGGGGAGCGAACAGGATTAGATACCCTGGTAGTCCATGCCGTAAACGTTGGGCGCTAGGTGTGGGACTCATTCC
ACGAGTTCCGTGCCGCAGCTAACGCATTAAGCGCCCCGCCTGGGGAGTACGGCCGCAAGGCTAAAACTCAAAGGAATTGACGGGGGCCCGCACAAGCGGCGGAGCATGTGG
ATTAATTCGATGCAACGCGAAGAACCTTACCAAGGCTTGACATATACCGGAAACACCTGGAGACAGGTGCCCCGCAAGGTCGGTATACAGGTGGTGCATGGTTGTCGTCAG
CTCGTGTCGTGAGATGTTGGGTTAAGTCCCGCAACGAGCGCAACCCTCGTTCTATGTTGCCAGCGCGTTATGGCGGGGACTCATAGAAGACTGCCGGGGTCAACTCGGAGG
AAGGTGGGGATGAGGTCAAATCATCATGCCCCTTATGTCTTGGGCTTCACACATGCTACAATGGCCGGTACAAAGGGCTGCGAAACCGCGAGGTGGAGCGAATCCCAAAAA
ACCGGTCTCAGTTCGGATTGGGGTCTGCAACTCGACCCCATGAAGTTGGAGTCGCTAGTAATCGCAGATCAGCAACGCTGCGGTGAATACGTTCCCGGGCCTTGTACACAC
CGCCCGTCAAGTCACGAAAGTCGGTAACACCCGAAGCCGGTGGCCCAACCCTTGTGGAGGGAGCCGTCGAAGGTGGGACTGGCGATTGGGACTAAGTCGTAACAAGGTAA

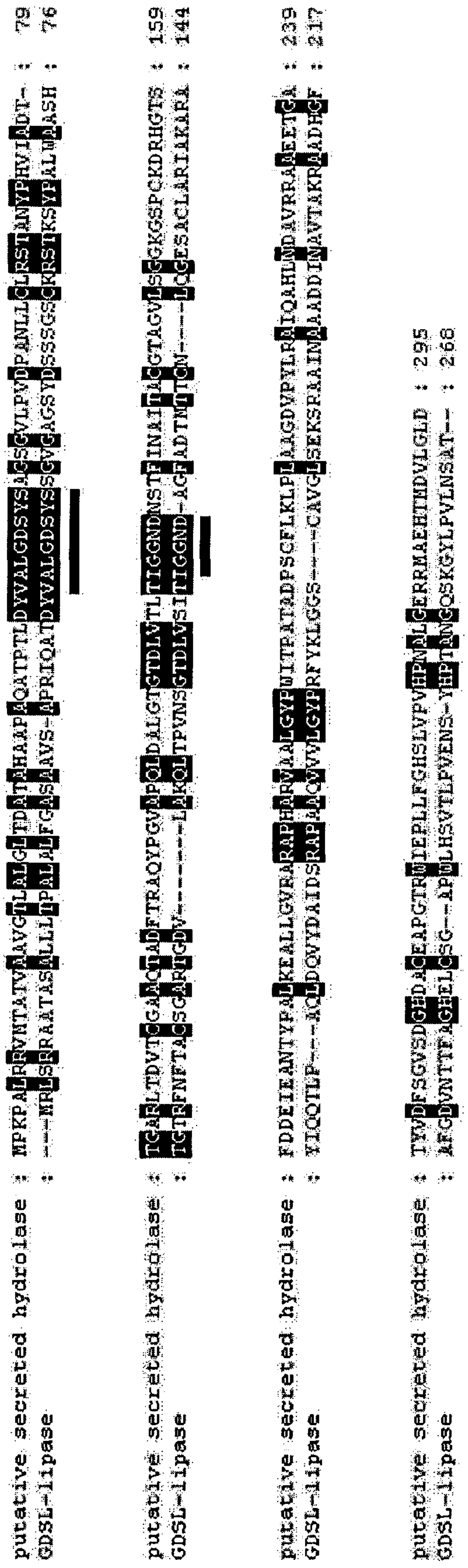

Figure 3

```
putative secreted hydrolase : MPKPALRRVNTATVAAVGTLALGLTDATAHAAPAQATPTLDYVALGDSYSAGSGVLPVDPANLLCLRSTANYPHVIADT- :  79
GDSL-lipase                 : ---MRLSRRAATASALLLTPALALFGASAAVS-APRIQATDYVALGDSYSSGVGAGSYDSSSGSCKRSTKSYPALWAASH :  76

putative secreted hydrolase : TGARLTDVTCGAACTADFTRAQYPGVAPQLDALGTGTDLVTLTIGGNDNSTFINAITACGTAGVLSGGKGSPCKDRHGTS : 159
GDSL-lipase                 : TGTRFNFTACSGARTGDV-------LAKQLTPVNSGTDLVSITIGGND-AGFADTMTTCN----LQGESACLARIAKARA : 144

putative secreted hydrolase : FDDEIEANTYPALKEALLGVRARAPHARVAALGYPWITPATADPSCFLKLPLAAGDVPYLRAIQAHLNDAVRRAAEETGA : 239
GDSL-lipase                 : YIQQTLP---AQLDQVYDAIDSRAPAAQVVVLGYPRFYKLGGS----CAVGLSEKSRAAINAAADDINAVTAKRAADHGF : 217

putative secreted hydrolase : TYVDFSGVSDGHDACEAPGTRWIEPLLFGHSLVPVHPNALGERRMAEHTHDVLGLD : 295
GDSL-lipase                 : AFGDVNTTFAGHELCSG--APWLHSVTLPVENS-YHPTANGQSKGYLPVLNSAT-- : 268
```

Figure 4

```
ACGCAGGCCGCGCCCGCCCCGGACGGCGACGCACCGGCATACGAACGCTATGTCGCCCTC  60
                                        G  D  A  P  A  Y  E  R  Y  V  A  L

GGCGACTCCTACACGGCGGCGCCGCTCGTGCCGAACCTCGACATCGCGGGCGGCTGCTAC  120
G  D  S  Y  T  A  A  P  L  V  P  N  L  D  I  A  G  G  C  Y

CGCTCGACGAACAATTACCCGAGCCTGCTCGCGCGCGAGCTCGGTGTGACGACGTTCGTC  180
R  S  T  N  N  Y  P  S  L  L  A  R  E  L  G  V  T  T  F  V

GACGCGAGCTGCTCCGGCGCGGACACGACGGACATGACGCAGAGCCAGCTCGCCGGCGTC  240
D  A  S  C  S  G  A  D  T  T  D  M  T  Q  S  Q  L  A  G  V

GCACCGCAGCTGGACAACCTCACCCCCGACACCGACCTCGTCACGCTGAGCATCGGCGGC  300
A  P  Q  L  D  N  L  T  P  D  T  D  L  V  T  L  S  I  G  G

AACGACTTCAACGTCTTCGGCACCCTCGTCGGCTATTGCACGACGCTGCGGGCGAGCGAC  360
N  D  F  N  V  F  G  T  L  V  G  Y  C  T  T  L  R  A  S  D

CCGACGGGCAGCCCGTGCCGGGACGAGATGCGCAGCGACGGGCAGGACCGGCTGCTCGCC  420
P  T  G  S  P  C  R  D  E  M  R  S  D  G  Q  D  R  L  L  A

GCCGTCAAAGAGACCCGGGCACGCATCGACGCGGTCATCGCCGAGATCGAGGAGCGCTCA  480
A  V  K  E  T  R  A  R  I  D  A  V  I  A  E  I  E  E  R  S

CCGGACGCGCGCATCCTCGTCGTCGGGTACCCGCAGATCGCGCCGCGTCAGGGCACCTGC  540
P  D  A  R  I  L  V  V  G  Y  P  Q  I  A  P  R  Q  G  T  C

CCCGACCTGCTGCCGCTCGCCGACGGTGACGTGTCGTATGCCGTGCAGGTCAACAAGCGC  600
P  D  L  L  P  L  A  D  G  D  V  S  Y  A  V  Q  V  N  K  R

CTCACCGACGCGCTGCGGCAGGCGGCCAAGAGCAACCAAGTGGAGTACGTCGACGTGTGG  660
L  T  D  A  L  R  Q  A  A  K  S  N  Q  V  E  Y  V  D  V  W

AAGGCGAGCCAGGGGCACGACATCTGCTCCGGCGACCCGTGGGTCAACGGGCAGGTCACC  720
K  A  S  Q  G  H  D  I  C  S  G  D  P  W  V  N  G  Q  V  T

GACATCACCCGGGCGCAGAACTACCACCCGTTCGCGAACGAGCAGCGCGCCATCGCCGAC  780
D  I  T  R  A  Q  N  Y  H  P  F  A  N  E  Q  R  A  I  A  D

CTGCTCATCGACGAGCTCACCTGAGGACCACCACCGGGGCATCACGATGTGCACTGCCGA  840
L  L  I  D  E  L  T  *
```

Figure 5

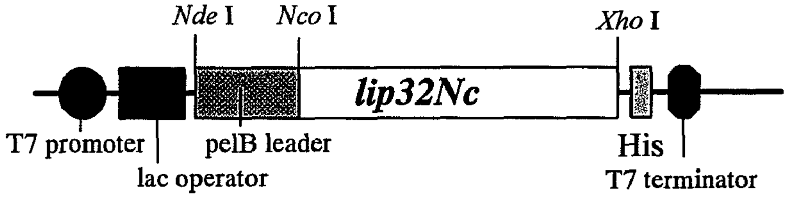

| BSA(mg/ml) | $OD_{595}$ |
| --- | --- |
| 1 | 0.043 |
| 10 | 0.201 |
| 50 | 0.574 |
| LP32(10 μl) | 0.117 |

Figure 8

```
1     CGCGGTTCATCGAGCAGATGGCACGGCGGGTCGACGGGCGCGTCGTGGCGCCCGAGCTCG
61    ACGACCTCGGCGCCGCGGTCGTCGGCAGCTATCTCGGGTCTCGGGGCTCGCGCGGTCCTG
121   GCGGTGGGTCCTACCGTGACCACTTCGGGGACCTGTTCGGCTCGCGGGGTTTCTGGGCGG
181   GCTGACCCGCACGACGGCGCGGCGTATCGTGGCGAGGGACGCACCCGCCATGAAGGGACC

241   TCACGGATGAGCTCGTCACGTCGTACCGTCCGCACCGCCGTCGCCGCTGCGTGGGCTGCT
             M  S  S  S  R  R  T  V  R  T  A  V  A  A  A  W  A  A

301   GCGCTGCTCGTCGCCGTGCCCGGTGCCCAGTCGATGGCCGCGACCGAGCGGGCGTCGGCG
       A  L  L  V  A  V  P  G  A  Q  S  M  A  A  T  E  R  A  S  A

361   CCCACGCAGGCCGCGCCCGCCCCGGACGGCGACGCACCGGCATACGAACGCTATGTCGCC
      P  T  Q  A  A  P  A  P  D  G  D  A  P  A  Y  E  R  Y  V  A

421   CTCGGCGACTCCTACACGGCGGCGCCGCTCGTGCCGAACCTCGACATCGCGGGCGGCTGC
      L  G  D  S  Y  T  A  A  P  L  V  P  N  L  D  I  A  G  G  C

481   TACCGCTCGACGAACAATTACCCGAGCCTGCTCGCGCGCGAGCTCGGTGTGACGACGTTC
      Y  R  S  T  N  N  Y  P  S  L  L  A  R  E  L  G  V  T  T  F

541   GTCGACGCGAGCTGCTCCGGCGCGGACACGACGGACATGACGCAGAGCCAGCTCGCCGGC
      V  D  A  S  C  S  G  A  D  T  T  D  M  T  Q  S  Q  L  A  G

601   GTCGCACCGCAGCTGGACAACCTCACCCCCGACACCGACCTCGTCACGCTGAGCATCGGC
      V  A  P  Q  L  D  N  L  T  P  D  T  D  L  V  T  L  S  I  G

661   GGCAACGACTTCAACGTCTTCGGCACCCTCGTCGGCTATTGCACGACGCTGCGGGCGAGC
      G  N  D  F  N  V  F  G  T  L  V  G  Y  C  T  T  L  R  A  S

721   GACCCGACGGGCAGCCCGTGCCGGGACGAGATGCGCAGCGACGGGCAGGACCGGCTGCTC
      D  P  T  G  S  P  C  R  D  E  M  R  S  D  G  Q  D  R  L  L

781   GCCGCCGTCAAAGAGACCCGGGCACGCATCGACGCGGTCATCGCCGAGATCGAGGAGCGC
      A  A  V  K  E  T  R  A  R  I  D  A  V  I  A  E  I  E  E  R

841   TCACCGGACGCGCGCATCCTCGTCGTCGGGTACCCGCAGATCGCGCCGCGTCAGGGCACC
      S  P  D  A  R  I  L  V  V  G  Y  P  Q  I  A  P  R  Q  G  T

901   TGCCCCGACCTGCTGCCGCTCGCCGACGGTGACGTGTCGTATGCCGTGCAGGTCAACAAG
      C  P  D  L  L  P  L  A  D  G  D  V  S  Y  A  V  Q  V  N  K

961   CGCCTCACCGACGCGCTGCGGCAGGCGGCCAAGAGCAACCAAGTGGAGTACGTCGACGTG
      R  L  T  D  A  L  R  Q  A  A  K  S  N  Q  V  E  Y  V  D  V

1021  TGGAAGGCGAGCCAGGGGCACGACATCTGCTCCGGCGACCCGTGGGTCAACGGGCAGGTC
      W  K  A  S  Q  G  H  D  I  C  S  G  D  P  W  V  N  G  Q  V

1081  ACCGACATCACCCGGGCGCAGAACTACCACCCGTTCGCGAACGAGCAGCGCGCCATCGCC
      T  D  I  T  R  A  Q  N  Y  H  P  F  A  N  E  Q  R  A  I  A

1141  GACCTGCTCATCGACGAGCTCACCTGAGGACCACCACCGGGGCATCACGATGTGCACTGC
      D  L  L  I  D  E  L  T  *

1201  CGA
```

Figure 9

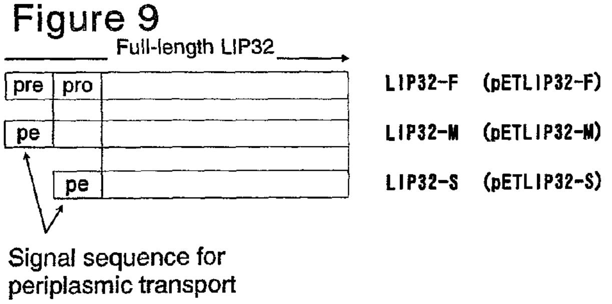

Figure 10

1 GTGAACAGGA CGAGCCCGAC GGAGAGCCCG AGGATCGGGA CGCGGTTGGC GCGGATGTCG ATGAGCGAGG TGTTCAGGGC CGCGGCATAG AGCAGCGGCG
101 GCAACAGCCC GAGCAGGACG ATGTCGGGCT CGAGCTCGGG GTGCGGGATG AACGGCAGGT ACGAGCCGAC GATGCCCACG CCGAGCAGCG CGATGGGCGA
201 CGGGAGGCCG AACGGGGCGC ACAGGCGCGC GACGACGATG ACGGTCACGG CGATCGCGGC GAGGGTGAGG GCGAGGTCCA CCGGCACATT GTCCGTCAAC
301 GGCGGAGGCC GTCGCCCCCG CTCCGGTTGC CGGGCAGATT ACCCGCCTGT AGCGTGGAAG TGGCGGCGTA TCCCCAGACG CTCGCTCGAC ACCCCTGCGG
401 AAGGTCTTCG ACAATGACGT CAGCACTGCT CCGACGAGCC CTCGCCCCTG CCCTCGCCCT CGGTCTCGCG GTCACCCTCG GCGCACCCGC GTCGGCCGGA
M T S A L L R R A L A P A L A L G L A V T L G A P A S A G

501 CCGGACTCCG TGCCCGGCAC CGCCGGTGCG ACGACCGTGA CCGACACCCC CGAGCCGCCT CGCCCCGCGT TCTACGAGCC GCCGGCGACG ATCCCCGGGA
P D S V P G T A G A T T V T D T P E P P R P A F Y E P P A T I P G T ·

601 CACCCGGCAC GGTCATCCGC ACCGAGTCCG CGACCTACCT CCTCGACCCG CTCGGCCTGT CGCAGACCGT CGTGACGTCG ACGCGGGTCA TGTACTCCTC
· P G T V I R T E S A T Y L L D P L G L S Q T V V T S T R V M Y S S ·

701 GCTCGACCGG CAGGGCCGGC CCATCGCCGT CACCGGCACG ATCCTCGAGC CGAAGGCGCC GTGGTTCGGG CTCGGTGCGC GACCGCTCAT CTCGTATGCC
·L D R Q G R P I A V T G T I L E P K A P W F G L G A R P L I S Y A

801 GTGGGCACCC AGGGCATGGG TGACCGGTGC GCGCCGTCGC GCCAGCTCGC CGAGTCCGTG ACCGAGTACG AAGCCGGGTT CATCTCCGGG CTCGTCACGC
V G T Q G M G D R C A P S R Q L A E S V T E Y E A G F I S G L V T R ·

901 GCGGGTACGC CGTTGCGTTC ACCGACTACC AGGGTCTCTC GACGCCCGGG ACGCACACCT ACATGAACCG CGTCGTCCAG GGACGCGCCN TCCTCGACAT
· G Y A V A F T D Y Q G L S T P G T H T Y M N R V V Q G R A X L D M ·

1001 GGCACGAGCA GCGCTGCGCC GCAACGGGAC CACGCTGACT GCGACGACTC CGGTGGGGAT CTACGGCTAC TCGCAGGGCG GCGGCGCGAG TGCGTCGGCG
·A R A A L R R N G T T L T A T T P V G I Y G Y S Q G G G A S A S A

1101 GCCGAGCTCA CCGCGACCTA TGCCCCGGAG CTGCGGGTCA AGGGTGCCCT CGCCGGTGCG GTTCCGGCGG ACCTCAAGGC GGTGGCCCAG AACCTCGATG
A E L T A T Y A P E L R V K G A L A G A V P A D L K A V A Q N L D G ·

1201 GCTCGCTGTA TGCCGAGTTC CTCAACTTCG CGCTGCTCGG CCTGTCGGCC GGGTACGGCA TCGACCTCAA CTCCTACCTC AACGAGCGGG GGCAGGCCGT
· S L Y A E F L N F A L L G L S A G Y G I D L N S Y L N E R G Q A V ·

1301 GGCCGCGGAC ACCGAGAACC ACTGCGTCAC CGACCTGCCG AAGGCGGCCT TCCAGCAGTC GTCGACGCTG ACGCGCGACG GTCGCGGTCT GCTCGACTAC
·A A D T E N H C V T D L P K A A F Q Q S S T L T R D G R G L L D Y

1401 CTCGACGAGG AGCCGTTCGC GTCGGTCATC GCCGACAACC GCATCGGCAC GATCAAGCCG TCCGTGCCCG TCCTCATCTC GCACTCGGTC GCCGACGACG
L D E E P F A S V I A D N R I G T I K P S V P V L I S H S V A D D V ·

1501 TCATCCCGTA CGCCGTGGGC AAGCAGCTCG CCCGCGACTG GTGCGCCAAG GGCGCCAACG TCCGCCTCTC GACGAACGTC GGCCCGACCC ACCTCGGCGG
· I P Y A V G K Q L A R D W C A K G A N V R L S T N V G P T H L G G ·

1601 GGCCCTGCCG TCGGCGGCGG AGAGCTACGC GTTCTTCGAG GCGCGCTTCG CCGGCGTGCC CCAGCTCAGC AACTGCTGGG CCGTCTAGCT GTACTCGGCC
·A L P S A A E S Y A F F E A R F A G V P Q L S N C W A V *

1701 GCGAGGTTGG TGACACGTAG GCGTTGACGA CGAGGAGAAC CTCCGGGTGA GGTGTGGATT GTCGAAGTCC CAACCGCCCG GAGGTTCTCG TGTCCCACGC
1801 TAACGCTCGT CTGAATGTTC ATGGTCGTCG TCTGTTGGTC GACCGCGTTC GCCGCCAAGG GTGGGCAGTG GCTCATGCCG CGAAGGCGAT GGGGATCTCG
1901 CGTCAGTGCG CTCACAGGTG GGTGTCCAGG TTCGACACCG AGGGTGAGGC CGGGTTGTCG GACCGGTCCT CGGCGCCGCA CTCCAGCCCT CGCCGCACCG
2001 CGACATCGGT CGAGGACGCG GTGGTGGCTG CCCGGCGGGA GCACCGGCGT GGTCAGGACT GGATCGGGCC TGAACTGGGT GTCCCGGCAC GCACGGTCAG
2101 CCGAATCCTG CGCCGCCATG ACCTGCCCTA CCTGCGGCAT TGCGACCCGC TCACCGGGGA CGTGATCCGC GCCTCGAAGA CCACCGCGGT CCGGTATGAA
2201 CGCGACCGCC CCGGCGAGCT CGTTCACGTT GATGTCAAGA AGATCGGGCG CATCCCCGAC GGTGGCGGGT GGAGAGCCCA CGGCCGCCAG ATGGGCTCGA
2301 CCGCGGCACG GAAGAAAGCG CGCATCGGGT ACGACTACGT GCACTCCATG GTCGATGACC ACTCCCGGCT CGCGTACAGC GAGATCCTCC CGGACGAGAC
2401 CGGCCCCACC TGCGCCGCGT TCATCCTGCG CGCCGCCGAA CACTTCGCCG CCCACGGCAT CGCCGCCATC GAACGCGTCA TCACCGACAA CCACTTCAGC
2501 TACCGCAAAA GCAACGACGT CAGGGACGCG ATGACCGCCA TGGGGGCCAC GCACAAGTTC ATCCGGCCCC ACTGCCC

Figure 11 pETLIP40HP

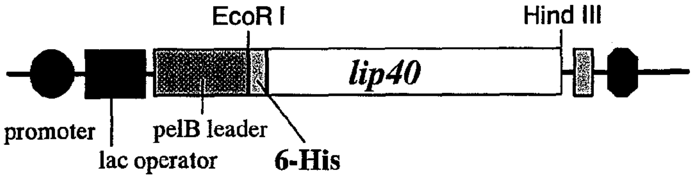

LIP32PH

LIP40HP

LIP32PH

LIP40HP

Figure 16

GPDSVPGTAGATTVTDTPEPPRPAFYEPPATIPGTPGTVIRTESATYLLDPLGLSQTVVTSTRVMYSSLD
RQGRPIAVTGTILEPKAPWFGLGARPLISYAVGTQGMGDRCAPSRQLAESVTEYEAGFISGLVTRGYAVA
FTDYQGLSTPGTHTYMNRVVQGRAXLDMARAALRRNGTTLTATTPVGIYGYSQGGGASASAAELTATYAP
ELRVKGALAGAVPADLKAVAQNLDGSLYAEFLNFALLGLSAGYGIDLNSYLNERGQAVAADTENHCVTDL
PKAAFQQSSTLTRDGRGLLDYLDEEPFASVIADNRIGTIKPSVPVLISHSVADDVIPYAVGKQLARDWCA
KGANVRLSTNVGPTHLGGALPSAAESYAFFEARFAGVPQLSNCWAV

LIPASE

CROSS REFERENCE TO RELATED APPLICATIONS

This application is the National Stage of International Application No. PCT/JP2006/324598, filed Dec. 8, 2006, and claims benefit of Japanese Application No. 2005-356936, filed Dec. 9, 2005, both of which are herein incorporated by reference in their entirety.

TECHNICAL FIELD

The present invention relates to a novel lipase. This lipase is produced by cells of a new *Tetrasphaera* sp. strain. This lipase has the ability to recognize a medium-chain fatty acid and/or a long-chain fatty acid as a substrate. This lipase can be immobilized on an anion exchange resin or a hydrophobic resin through adsorption, and can be used as an immobilized enzyme. This lipase is useful in fields such as production of digestants and/or flavorings, production of clinical laboratory reagents, detergent enzymes and/or fats, as well as production of optically active intermediates for agricultural chemicals and pharmaceutical preparations.

BACKGROUND ART

Lipases have been demonstrated to be excellent biocatalysts for synthesis and decomposition of various esters, transesterification, and optical resolution of racemic mixtures. In fact, lipases have been used for production of digestants and/or flavorings, production of clinical laboratory reagents, detergent enzymes and/or fats, as well as production of optically active intermediates for agricultural chemicals and pharmaceutical preparations.

Among lipases, animal pancreatic lipases are well known, but it is primarily microbial lipases that are often used industrially. For most of these lipases, their genes have been cloned and the amino acid sequences thereof are also known (*Candida rugosa*: Non-patent Document 1; *Rhizopus delemar*: Non-patent Document 2; *Bacillus subtilis*: Non-patent Document 3; *Staphylococcus aureus*: Non-patent Document 4; and *Pseudomonas aeruginosa*: Non-patent Document 5).

Lipases produced by filamentous fungi or bacteria such as *Bacillus* spp., *Staphylococcus* spp. or *Pseudomonas* spp. are used for industrial purposes. These lipases principally target a higher fatty acid (containing 16 or more carbon atoms) as a substrate, while those targeting a short-chain fatty acid (containing 6 or less carbon atoms) as a substrate are called esterases. No lipase is known which successfully recognizes a medium-chain fatty acid and shows not only hydrolytic activity, but also esterification activity.

Triglycerides having medium-chain fatty acids are hydrolyzed by the action of not only pancreatic lipases, but also gastric lipases, indicating that lipases are also advantageous in digestion and/or absorption of triglycerides (Non-patent Document 6). Moreover, the absorbed medium-chain fatty acids are less likely to be resynthesized into triglycerides in intestinal tract cells of the small intestine. They are transported through the portal vein to the liver and burned as energy. In contrast, higher fatty acids are resynthesized in intestinal tract cells, absorbed through the lymph and transported to the liver, and in some cases may be accumulated as fat. This means that higher fatty acids are accumulative in the body, whereas medium-chain fatty acids are not accumulative. For this reason, healthy fats and oils are produced by transesterification between medium-chain fatty acid triglycerides and common edible fats and oils.

Non-patent Document 1: Kawaguchi et al., Nature, 341, 164-166 (1989)

Non-patent Document 2: Haas et al., Gene, 109, 107-113 (1991)

Non-patent Document 3: Dartois et al., B. B. A., 1131, 253-260 (1992)

Non-patent Document 4: Lee et al., J. Bacteriol., 164, 288-293 (1985)

Non-patent Document 5: Wohlfarth et al., J. General Microbiology, 138, 1325-1335, (1992)

Non-patent Document 6: I. Ikeda, Y. Tomari, M. Sugano, S. Watanabe, and J. Nagata: Lipids, 26, 369-373 (1991)

DISCLOSURE OF THE INVENTION

Problems to be Solved by the Invention

However, medium-chain fatty acid esters other than triglycerides have not been produced with lipases on an industrial scale. Since medium-chain fatty acids do not cause fat accumulation, food materials esterified with medium-chain fatty acids may be materials with reduced problems such as obesity.

Means for Solving the Problems

The inventors of the present invention have made extensive and intensive efforts to study lipases. As a result, the inventors have isolated and purified a novel lipase with a molecular weight of about 32 kDa or about 40 kDa from the culture supernatant of cells of a new *Tetrasphaera* sp. strain, and have further found that these lipases are novel ones successfully recognizing a medium-chain fatty acid as a substrate, thereby completing the present invention.

I. Novel Lipase

The present invention provides a polynucleotide or a homolog thereof, which encodes a lipase with a molecular weight of about 32 kDa produced by a strain belonging to the genus *Tetrasphaera* (preferably belonging to the same species as *Tetrasphaera* sp. strain NITE P-154, more preferably being *Tetrasphaera* sp. strain NITE P-154), i.e., a polynucleotide comprising ($A_1$), ($B_1$), ($C_1$), ($D_1$), ($B_1$), ($F_1$) or ($G_1$) shown below:

($A_1$) a polynucleotide which consists of all of the nucleotide sequence shown in SEQ ID NO: 10 or a part thereof covering at least nucleotides 25-801;

($B_1$) a polynucleotide which is hybridizable under stringent conditions with a polynucleotide consisting of a nucleotide sequence complementary to the nucleotide sequence of the polynucleotide shown in ($A_1$) and which encodes a protein having lipase activity;

($C_1$) a polynucleotide which consists of a nucleotide sequence comprising substitution, deletion, insertion and/or addition of one or several nucleotides in the nucleotide sequence of the polynucleotide shown in ($A_1$) and which encodes a protein having lipase activity;

($D_1$) a polynucleotide which shares an identity of at least 80% or more with the nucleotide sequence of the polynucleotide shown in ($A_1$) and which encodes a protein having lipase activity;

($E_1$) a polynucleotide which encodes a protein consisting of the amino acid sequence shown in SEQ ID NO: 11;

($F_1$) a polynucleotide which encodes a protein consisting of an amino acid sequence comprising substitution, deletion, insertion and/or addition of one or several amino acids in the amino acid sequence shown in SEQ ID NO: 11 and having lipase activity; or (G$_1$) a polynucleotide which encodes a protein consisting of an amino acid sequence sharing an identity of at least 80% or more with the amino acid sequence shown in SEQ ID NO: 11 and having lipase activity.

SEQ ID NO: 10 shows the nucleotide sequence of a polynucleotide which encodes a lipase with a molecular weight of about 32 kDa produced by *Tetrasphaera* sp. strain NITE P-154, while SEQ ID NO: 11 shows the amino acid sequence of the lipase. Likewise, SEQ ID NO: 15 shows the nucleotide sequence of genomic DNA which contains a polynucleotide encoding the lipase, while SEQ ID NO: 16 shows an amino acid sequence including a sequence located upstream of SEQ ID NO: 11.

As used herein, "nucleotides 25-801" in relation to SEQ ID NO: 10 can be interchanged with "nucleotides 388-1164" in relation to SEQ ID NO: 15, unless otherwise specified. As used herein, "amino acid sequence of SEQ ID NO: 11" can be interchanged with "amino acid sequence covering amino acids 48-306 of SEQ ID NO: 16," unless otherwise specified. In the present invention, a polynucleotide consisting of a part of the nucleotide sequence shown in SEQ ID NO: 10 which covers at least nucleotides 25-801 can be replaced with a polynucleotide consisting of a part of the nucleotide sequence shown in SEQ ID NO: 15 which covers at least nucleotides 388-1164 (e.g., a polynucleotide consisting of a part of the nucleotide sequence shown in SEQ ID NO: 15 which covers nucleotides 247-1167). Likewise, a protein consisting of the amino acid sequence shown in SEQ ID NO: 11 (or a polynucleotide encoding the same) can be replaced with a protein consisting of all or part of the amino sequence shown in SEQ ID NO: 16 (preferably a protein consisting of amino acids 32-306, more preferably amino acids 48-306) (or a polynucleotide encoding the same). Such polynucleotides and proteins also fall within the scope of the present invention. Amino acids 1-47 of SEQ ID NO: 16 appear to constitute a pre-pro sequence. Amino acids 1-31 serve as a pre-sequence which is a secretion signal, while amino acids 32-47 is deduced as a pro-sequence which may be cleaved after secretion probably by the action of another protein. Thus, a mature protein essential for serving as a lipase lies in the sequence downstream of amino acid 48; it would be suitable to remove the pre-pro sequence if the lipase is expressed in a heterologous expression system such as *E. coli.*

Preferred examples of the polynucleotide of the present invention or a homolog thereof, which encodes a lipase with a molecular weight of about 32 kDa, are as follows.

A polynucleotide selected from (A$_1$'), (B$_1$'), (C$_1$'), (D$_1$'), (B$_1$'), (F$_1$') or (G$_1$') shown below:

(A$_1$') a polynucleotide which consists of all of the nucleotide sequence shown in SEQ ID NO: 10 or a part thereof covering nucleotides 25-801;

(B$_1$') a polynucleotide which is hybridizable under stringent conditions with a polynucleotide consisting of a nucleotide sequence complementary to the nucleotide sequence of the polynucleotide shown in (A$_1$') and which encodes a protein having lipase activity;

(C$_1$') a polynucleotide which consists of a nucleotide sequence comprising substitution, deletion, insertion and/or addition of one or several nucleotides in the nucleotide sequence of the polynucleotide shown in (A$_1$') and which encodes a protein having lipase activity;

(D$_1$') a polynucleotide which shares an identity of at least 80% or more with the nucleotide sequence of the polynucleotide shown in (A$_1$') and which encodes a protein having lipase activity;

(E$_1$') a polynucleotide which encodes a protein consisting of the amino acid sequence shown in SEQ ID NO: 11;

(F$_1$') a polynucleotide which encodes a protein consisting of an amino acid sequence comprising substitution, deletion, insertion and/or addition of one or several amino acids in the amino acid sequence shown in SEQ ID NO: 11 and having lipase activity; or (G$_1$') a polynucleotide which encodes a protein consisting of an amino acid sequence sharing an identity of at least 80% or more with the amino acid sequence shown in SEQ ID NO: 11 and having lipase activity.

A polynucleotide comprising (A$_2$), (B$_2$), (C$_2$), (D$_2$), (B$_2$), (F$_2$) or (G$_2$) shown below:

(A$_2$) a polynucleotide which consists of all of the nucleotide sequence shown in SEQ ID NO: 15 or a part thereof covering at least nucleotides 247-1167 or 388-1164;

(B$_2$) a polynucleotide which is hybridizable under stringent conditions with a polynucleotide consisting of a nucleotide sequence complementary to the nucleotide sequence of the polynucleotide shown in (A$_2$) and which encodes a protein having lipase activity;

(C$_2$) a polynucleotide which consists of a nucleotide sequence comprising substitution, deletion, insertion and/or addition of one or several nucleotides in the nucleotide sequence of the polynucleotide shown in (A$_2$) and which encodes a protein having lipase activity;

(D$_2$) a polynucleotide which shares an identity of at least 80% or more with the nucleotide sequence of the polynucleotide shown in (A$_2$) and which encodes a protein having lipase activity;

(E$_2$) a polynucleotide which encodes a protein consisting of all of the amino acid sequence shown in SEQ ID NO: 16 or a part thereof covering at least amino acids 48-306;

(F$_2$) a polynucleotide which encodes a protein consisting of an amino acid sequence comprising substitution, deletion, insertion and/or addition of one or several amino acids in the amino acid sequence of the protein shown in (E$_2$) and having lipase activity; or (G$_2$) a polynucleotide which encodes a protein consisting of an amino acid sequence sharing an identity of at least 80% or more with the amino acid sequence of the protein shown in (E$_2$) and having lipase activity.

A polynucleotide selected from (A$_2$'), (B$_2$'), (C$_2$'), (D$_2$'), (E$_2$'), (F$_2$') or (G$_2$') shown below:

(A$_2$') a polynucleotide which consists of all of the nucleotide sequence shown in SEQ ID NO: 15 or a part thereof covering nucleotides 247-1167 or 388-1164;

(B$_2$') a polynucleotide which is hybridizable under stringent conditions with a polynucleotide consisting of a nucleotide sequence complementary to the nucleotide sequence of the polynucleotide shown in (A$_2$') and which encodes a protein having lipase activity;

(C$_2$') a polynucleotide which consists of a nucleotide sequence comprising substitution, deletion, insertion and/or addition of one or several nucleotides in the nucleotide sequence of the polynucleotide shown in (A$_2$') and which encodes a protein having lipase activity;

(D$_2$') a polynucleotide which shares an identity of at least 80% or more with the nucleotide sequence of the polynucleotide shown in (A$_2$') and which encodes a protein having lipase activity;

($E_2'$) a polynucleotide which encodes a protein consisting of all of the amino acid sequence shown in SEQ ID NO: 16 or a part thereof covering at least amino acids 48-306;

($F_2'$) a polynucleotide which encodes a protein consisting of an amino acid sequence comprising substitution, deletion, insertion and/or addition of one or several amino acids in the amino acid sequence of the protein shown in ($E_2'$) and having lipase activity; or ($G_2'$) a polynucleotide which encodes a protein consisting of an amino acid sequence sharing an identity of at least 80% or more with the amino acid sequence of the protein shown in ($E_2'$) and having lipase activity.

The present invention also provides a gene or a homolog thereof, which encodes a lipase with a molecular weight of about 40 kDa produced by a strain belonging to the genus *Tetrasphaera* (preferably belonging to the same species as *Tetrasphaera* sp. strain NITE P-154, more preferably being *Tetrasphaera* sp. strain NITE P-154), i.e., a polynucleotide comprising ($H_2$), ($I_2$), ($J_2$), ($K_2$), ($L_2$), ($M_2$) or ($N_2$) shown below:

($H_2$) a polynucleotide which consists of all of the nucleotide sequence shown in SEQ ID NO: 28 or a part thereof covering at least nucleotides 414-1688 or 498-1685;

($I_2$) a polynucleotide which is hybridizable under stringent conditions with a polynucleotide consisting of a nucleotide sequence complementary to the nucleotide sequence of the polynucleotide shown in ($H_2$) and which encodes a protein having lipase activity;

($J_2$) a polynucleotide which consists of a nucleotide sequence comprising substitution, deletion, insertion and/or addition of one or several nucleotides in the nucleotide sequence of the polynucleotide shown in ($H_2$) and which encodes a protein having lipase activity;

($K_2$) a polynucleotide which shares an identity of at least 80% or more with the nucleotide sequence of the polynucleotide shown in ($H_2$) and which encodes a protein having lipase activity;

($L_2$) a polynucleotide which encodes a protein consisting of all of the amino acid sequence shown in SEQ ID NO: 29 or a part thereof covering at least amino acids 29-424;

($M_2$) a polynucleotide which encodes a protein consisting of an amino acid sequence comprising substitution, deletion, insertion and/or addition of one or several amino acids in the amino acid sequence of the protein shown in ($L_2$) and having lipase activity; or ($N_2$) a polynucleotide which encodes a protein consisting of an amino acid sequence sharing an identity of at least 80% or more with the amino acid sequence of the protein shown in ($L_2$) and having lipase activity.

SEQ ID NO: 28 shows the nucleotide sequence of a gene which encodes a lipase with a molecular weight of about 40 kDa produced by *Tetrasphaera* sp. strain NITE P-154, while SEQ ID NO: 29 shows the amino acid sequence of the lipase.

Preferred examples of the polynucleotide of the present invention or a homolog thereof, which encodes a lipase with a molecular weight of about 40 kDa, are as follows.

A polynucleotide selected from ($H_2'$), ($I_2'$), ($J_2'$), ($K_2'$), ($L_2'$), ($M_2'$) or ($N_2'$) shown below:

($H_2'$) a polynucleotide which consists of all of the nucleotide sequence shown in SEQ ID NO: 28 or a part thereof covering nucleotides 414-1688 or 498-1685;

($I_2'$) a polynucleotide which is hybridizable under stringent conditions with a polynucleotide consisting of a nucleotide sequence complementary to the nucleotide sequence of the polynucleotide shown in ($H_2'$) and which encodes a protein having lipase activity;

($J_2'$) a polynucleotide which consists of a nucleotide sequence comprising substitution, deletion, insertion and/or addition of one or several nucleotides in the nucleotide sequence of the polynucleotide shown in ($H_2'$) and which encodes a protein having lipase activity;

($K_2'$) a polynucleotide which shares an identity of at least 80% or more with the nucleotide sequence of the polynucleotide shown in ($H_2'$) and which encodes a protein having lipase activity;

($L_2'$) a polynucleotide which encodes a protein consisting of all of the amino acid sequence shown in SEQ ID NO: 29 or a part thereof covering amino acids 29-424;

($M_2'$) a polynucleotide which encodes a protein consisting of an amino acid sequence comprising substitution, deletion, insertion and/or addition of one or several amino acids in the amino acid sequence of the protein shown in ($L_2'$) and having lipase activity; or ($N_2'$) a polynucleotide which encodes a protein consisting of an amino acid sequence sharing an identity of at least 80% or more with the amino acid sequence of the protein shown in ($L_2'$) and having lipase activity.

As used herein, the term "lipase" is intended to mean an enzyme that hydrolyzes glycerol esters to release fatty acids, unless otherwise specified. As used herein to describe a protein, the phrase "having lipase activity" (or the term "lipase") is intended to mean that the protein (or lipase) at least has the ability to hydrolyze esters of glycerol with fatty acids, preferably the ability to hydrolyze esters with medium-chain fatty acids and/or esters with long-chain fatty acids, and more preferably the ability to hydrolyze both esters with medium-chain fatty acids and esters with long-chain fatty acids, unless otherwise specified. Such a protein having lipase activity (or lipase) preferably has the ability to catalyze the transfer reaction (esterification or transesterification) of fatty acids, and more preferably has the ability to catalyze the transfer reaction of medium-chain fatty acids.

To evaluate whether a protein has the ability to hydrolyze esters of glycerol with medium-chain or long-chain fatty acids, the protein may be subjected to a test for measuring the ability to hydrolyze 4-methyl unberyferylcaprylate (MU-C8) or 4-methyl unberyferyloleate (MU-C18), for example, as shown in the Example section described later. Likewise, to evaluate whether a protein has the ability to catalyze the transfer reaction of medium-chain fatty acids, the protein may be subjected to an experiment for esterification between 3-phenyl-1-propanol or 1-phenyl-2-propanol and tricaprilin (MCT), for example, as shown in the Example section described later.

When a protein (or lipase) has the ability to hydrolyze esters of fatty acids or the ability to catalyze the transfer reaction of fatty acids, such a protein (or lipase) can also be expressed herein as having the ability to recognize the fatty acid as a substrate, unless otherwise specified.

The protein of the present invention with a molecular weight of about 32 kDa or about 40 kDa, which is produced by a strain belonging to the genus *Tetrasphaera* (preferably belonging to the same species as *Tetrasphaera* sp. strain NITE P-154, more preferably being *Tetrasphaera* sp. strain NITE P-154), at least has the ability to hydrolyze 4-methyl unberyferylcaprylate (MU-C8). The latter protein further has the ability to hydrolyze 4-methyl unberyferyloleate (MU-C18) and is also confirmed to have the ability to generate a corresponding caprylic acid ester from tricaprilin and 3-phenyl-1-propanol or 1-phenyl-2-propanol (see Example 1). Thus, both proteins can be regarded as having lipase activity. More specifically, the former can be regarded as having the ability to hydrolyze esters with medium-chain fatty acids (i.e., the ability to recognize a medium-chain fatty acid as a substrate), while the latter can be regarded as having the ability to hydrolyze esters with medium-chain fatty acids and with long-chain fatty acids (i.e., the ability to recognize both a medium-chain fatty acid and a long-chain fatty acid as substrates) and also as having the ability to catalyze the transfer reaction (particularly esterification) of medium-chain fatty acids.

As used herein, the term "medium-chain fatty acid" refers to a saturated or unsaturated fatty acid containing 7 to 15 carbon atoms, unless otherwise specified. Examples of a medium-chain fatty acid include caprylic acid, capric acid and lauric acid.

As used herein, the term "long-chain fatty acid" refers to a saturated or unsaturated fatty acid containing 16 or more carbon atoms, unless otherwise specified. Examples of a long-chain fatty acid include palmitic acid, stearic acid, palmitoleic acid, oleic acid, linolic acid, α-linolenic acid and γ-linolenic acid.

When used herein in relation to glycerol and fatty acids, the term "ester" may be used to mean not only a triacylglycerol, but also a diacylglycerol or a monoacylglycerol (the latter two may also be collectively referred to as a partial acylglycerol), unless otherwise specified.

As used herein, the term "stringent conditions" refers to conditions of 6 M urea, 0.4% SDS and 0.5×SSC, or hybridization conditions equivalent thereto, unless otherwise specified. If necessary, more stringent conditions (e.g., 6 M urea, 0.4% SDS and 0.1×SSC) or hybridization conditions equivalent thereto may be applied in the present invention. Under each of these conditions, the temperature may be set to about 40° C. or higher. When more stringent conditions are required, the temperature may be set to a higher value, for example about 50° C. and more particularly about 65° C.

Moreover, the expression "nucleotide sequence comprising substitution, deletion, insertion and/or addition of one or several nucleotides" as used herein does not provide any limitation on the number of nucleotides to be substituted, deleted, inserted and/or added, as long as a protein encoded by a polynucleotide consisting of such a nucleotide sequence has desired functions. The number of such nucleotides is around 1 to 9 or around 1 to 4, or alternatively, a larger number of nucleotides may be substituted, deleted, inserted and/or added as long as such a mutation allows encoding of the same or a functionally similar amino acid sequence. Likewise, the expression "amino acid sequence comprising substitution, deletion, insertion and/or addition of one or several amino acids" as used herein does not provide any limitation on the number of amino acids to be substituted, deleted, inserted and/or added, as long as a protein having such an amino acid sequence has desired functions. The number of such amino acids is around 1 to 9 or around 1 to 4, or alternatively, a larger number of amino acids may be substituted, deleted, inserted and/or added as long as such a mutation provides a functionally similar amino acid. Means for preparing a polynucleotide which has such a nucleotide sequence or encodes such an amino acid sequence are well known to those skilled in the art.

As used herein to describe a nucleotide sequence, the term "high identity" refers to a sequence identity of at least 50% or more, preferably 70% or more, more preferably 80% or more, even more preferably 90% or more, and most preferably 95% or more.

As used herein to describe an amino acid sequence, the term "high identity" refers to a sequence identity of at least 50% or more, preferably 70% or more, more preferably 80% or more, even more preferably 90% or more, and most preferably 95% or more. The identity of the amino acid sequence shown in SEQ ID NO: 11 with the amino acid sequences of known lipases is shown in Table 4 in the Example section. Likewise, the identity of the amino acid sequence shown in SEQ ID NO: 28 with a known sequence is described in Example 8.

Search and analysis for identity between nucleotide or amino acid sequences may be accomplished by using any algorithm or program (e.g., BLASTN, BLASTP, BLASTX, ClustalW) well known to those skilled in the art. In the case of using a program, parameters may be set as required by those skilled in the art, or alternatively, default parameters specific for each program may be used. Detailed procedures for such analysis are also well known to those skilled in the art.

To describe the molecular weight of a protein or lipase, a value determined by SDS-PAGE is used herein, unless otherwise specified (see Example 1, FIG. 2).

The polynucleotide of the present invention can be obtained from natural products by using techniques such as hybridization and polymerase chain reaction (PCR).

More specifically, genomic DNA (gDNA) is prepared in a routine manner (e.g., DNeasy Tissue Kit (QIAGEN)) from a strain belonging to the genus *Tetrasphaera* (preferably belonging to the same species as *Tetrasphaera* sp. strain NITE P-154, more preferably being *Tetrasphaera* sp. strain NITE P-154). Alternatively, total RNA is prepared in a routine manner (e.g., RNeasy Plant isolation Kit (QIAGEN)) from cells of the above strain, followed by reverse transcription (1st strand cDNA synthesis) using the total RNA as a template in a routine manner (e.g., SuperScript II Reverse Transcriptase (Invitrogen)).

To obtain a desired polynucleotide, a 5'-primer is designed based on the N-terminal sequence of the 32 kDa lipase protein. Further, a 3'-primer is designed based on a sequence conserved among putative proteins which are derived from relatively closely related *Streptomyces* spp. and share identity with the above N-terminal amino acid residues. A lip32 gene fragment is amplified by degenerate PCR with the above primer set using Strain #375 cDNA as a template to determine a partial nucleotide sequence. After digestion with an appropriate restriction enzyme(s), the cyclized Strain #375 gDNA is further used as a template to obtain the nucleotide sequence information of neighboring regions by inverse PCR with primers designed in the outward direction on the template sequence. In this way, a nucleotide sequence of about 900 by in total is determined for the lip32 region gDNA.

The polynucleotide of the present invention encompasses DNA, including genomic DNA, cDNA and chemically synthesized DNA. These DNAs may be either single-stranded or double-stranded.

Preferred examples of the polynucleotide of the present invention are those derived from the genus *Tetrasphaera*.

The present invention also provides a recombinant vector carrying the polynucleotide of the present invention, as well as a transformant (e.g., a transformed *E. coli*, yeast or insect cell) transformed with the recombinant vector. The present invention further provides a transformation method comprising the step of transforming a host (e.g., an *E. coli*, yeast or insect cell) by using the polynucleotide of the present invention (e.g., the step of transforming a host with the recombinant vector of the present invention).

There is no particular limitation on the vector into which the polynucleotide of the present invention is inserted, as long as it allows expression of the insert in a host. Such a vector generally has a promoter sequence, a terminator sequence, a sequence for inducible expression of an insert in response to external stimulation, a sequence recognized by a restriction enzyme for insertion of a target gene, and a sequence encoding a marker for transformant selection. To create such a recombinant vector and to effect transformation with such a recombinant vector, techniques well known to those skilled in the art may be applied.

The present invention also provides a lipase with a molecular weight of about 32 kDa or a homolog thereof, which is produced by a strain belonging to the genus *Tetrasphaera* (preferably belonging to the same species as *Tetrasphaera* sp. strain NITE P-154, more preferably being *Tetrasphaera* sp. strain NITE P-154), i.e., a protein comprising ($e_1$), ($f_1$) or ($g_1$) shown below:

($e_1$) a protein which consists of the amino acid sequence shown in SEQ ID NO: 11;

($f_1$) a protein which consists of an amino acid sequence comprising substitution, deletion, insertion and/or addition of one or several amino acids in the amino acid sequence shown in SEQ ID NO: 11 and which has lipase activity; or ($g_1$) a protein which consists of an amino acid sequence sharing an identity of at least 80% or more with the amino acid sequence shown in SEQ ID NO: 11 and which has lipase activity.

Preferred examples of the lipase of the present invention with a molecular weight of about 32 kDa or a homolog thereof are the following proteins.

A protein selected from ($e_1$'), ($f_1$') or ($g_1$') shown below:

($e_1$') a protein which consists of the amino acid sequence shown in SEQ ID NO: 11;

($f_1$') a protein which consists of an amino acid sequence comprising substitution, deletion, insertion and/or addition of one or several amino acids in the amino acid sequence shown in SEQ ID NO: 11 and which has lipase activity; or ($g_1$') a protein which consists of an amino acid sequence sharing an identity of at least 80% or more with the amino acid sequence shown in SEQ ID NO: 11 and which has lipase activity.

A protein comprising ($e_2$), ($f_2$) or ($g_2$) shown below:

($e_2$) a protein which consists of all of the amino acid sequence shown in SEQ ID NO: 16 or a part thereof covering at least amino acids 48-306;

($f_2$) a protein which consists of an amino acid sequence comprising substitution, deletion, insertion and/or addition of one or several amino acids in the amino acid sequence of the protein shown in ($e_2$) and which has lipase activity; or ($g_2$) a protein which consists of an amino acid sequence sharing an identity of at least 80% or more with the amino acid sequence of the protein shown in ($e_2$) and which has lipase activity.

A protein selected from ($e_2$'), ($f_2$') or ($g_2$') shown below:

($e_2$') a protein which consists of all of the amino acid sequence shown in SEQ ID NO: 16 or a part thereof covering amino acids 48-306;

($f_2$') a protein which consists of an amino acid sequence comprising substitution, deletion, insertion and/or addition of one or several amino acids in the amino acid sequence of the protein shown in ($e_2$') and which has lipase activity; or ($g_2$') a protein which consists of an amino acid sequence sharing an identity of at least 80% or more with the amino acid sequence of the protein shown in ($e_2$') and which has lipase activity.

This lipase with a molecular weight of about 32 kDa has the ability to recognize a medium-chain fatty acid as a substrate. Under the conditions shown in Example 11, this lipase has an optimum temperature of about 40° C. and an optimum pH of around 7.0.

The present invention also provides a lipase with a molecular weight of about 40 kDa or a homolog thereof, which is produced by a strain belonging to the genus *Tetrasphaera* (preferably belonging to the same species as *Tetrasphaera* sp. strain NITE P-154, more preferably being *Tetrasphaera* sp. strain NITE P-154), i.e., a protein comprising ($l_1$), ($m_1$) or ($n_1$) shown below:

($l_1$) a protein which consists of the amino acid sequence shown in SEQ ID NO: 35;

($m_1$) a protein which consists of an amino acid sequence comprising substitution, deletion, insertion and/or addition of one or several amino acids in the amino acid sequence shown in SEQ ID NO: 35 and which has lipase activity; or ($n_1$) a protein which consists of an amino acid sequence sharing an identity of at least 80% or more with the amino acid sequence shown in SEQ ID NO: 35 and which has lipase activity.

SEQ ID NO: 35 and FIG. 16 each show the mature protein amino acid sequence of a lipase with a molecular weight of about 40 kDa produced by *Tetrasphaera* sp. strain NITE P-154.

Preferred examples of the lipase of the present invention with a molecular weight of about 40 kDa or a homolog thereof are the following proteins.

A protein selected from ($l_1$), ($m_1$) or ($n_1$) shown above.

A protein comprising ($l_2$), ($m_2$) or ($n_2$) shown below:

($l_2$) a protein which consists of all of the amino acid sequence shown in SEQ ID NO: 29 or a part thereof covering at least amino acids 29-424;

($m_2$) a protein which consists of an amino acid sequence comprising substitution, deletion, insertion and/or addition of one or several amino acids in the amino acid sequence of the protein shown in ($l_2$) and which has lipase activity; or ($n_2$) a protein which consists of an amino acid sequence sharing an identity of at least 80% or more with the amino acid sequence of the protein shown in ($l_2$) and which has lipase activity.

A protein selected from ($l_2$'), ($m_2$') or ($n_2$') shown below:

($l_2$') a protein which consists of all of the amino acid sequence shown in SEQ ID NO: 29 or a part thereof covering amino acids 29-424;

($m_2$') a protein which consists of an amino acid sequence comprising substitution, deletion, insertion and/or addition of one or several amino acids in the amino acid sequence of the protein shown in ($l_2$') and which has lipase activity; or ($n_2$') a protein which consists of an amino acid sequence sharing an identity of at least 80% or more with the amino acid sequence of the protein shown in ($l_2$') and which has lipase activity.

This lipase with a molecular weight of about 40 kDa has the ability to recognize both a medium-chain fatty acid and a long-chain fatty acid as substrates. Under the conditions shown in Example 11, this lipase has an optimum temperature of about 45° C. to 50° C. and an optimum pH of around 7.0.

The above protein or lipase may be isolated and purified from a culture supernatant obtained by culturing a strain belonging to the genus *Tetrasphaera* (preferably belonging to the same species as *Tetrasphaera* sp. strain NITE P-154, more preferably being *Tetrasphaera* sp. strain NITE P-154) in a commercially available medium (e.g., Marine broth 2216 (Difco); Marine broth is a liquid medium characterized by having a salt content of about 2%).

Details are as follows. First, the cell suspension is inoculated at 0.1% to 5% into the medium and cultured at 10° C. to 40° C. for 2 to 10 days. The culture supernatant is subjected to column chromatography using 0.01 to 1 part of a hydrophobic gel (e.g., ϕ-Sepharose) equilibrated with Tris-HCl buffer containing calcium chloride and magnesium chloride. After washing with the above buffer, the column is eluted with the above buffer supplemented with 1% nonionic surfactant (e.g., Triton X-100) to obtain a fraction having lipase activity. This lipase fraction is diluted with 10 parts of the above buffer and then adsorbed onto 0.001 to 1 part of an anion exchange gel (e.g., Q-Sepharose). After washing with the above buffer supplemented with 0.1% amphoteric surfactant (e.g., 3-[(3-Cholamidopropyl)dimethylammonio]-1-propanesulfonate (CHAPS)), the gel is eluted with a concentration gradient of aqueous sodium chloride to obtain a lipase active fraction. This lipase fraction is subjected to high performance liquid chromatography (HPLC) on an anion exchange column (e.g., HiTrapQ), followed by gradient elution with a concentration gradient of aqueous sodium chloride to obtain a fraction which has lipase activity and is confirmed for the presence of a protein with a molecular weight of about 32 kDa or about 40 kDa. For more detailed procedures, reference may be made to Example 1 described herein later.

The above protein or lipase may be obtained as a recombinant protein from a transformant (e.g., a transformed *E. coli* cell) transformed with a recombinant vector carrying the polynucleotide of the present invention.

Details are as follows. First, the nucleotide sequence of a gene to be used for *E. coli* expression systems is amplified by PCR with an appropriate primer set, followed by cloning and sequencing to confirm the nucleotide sequence. The cloned DNA fragment is extracted by digestion with an appropriate restriction enzyme(s) and then integrated into an *E. coli* protein expression vector. This vector is used to transform *E. coli* cells to thereby induce protein expression. *E. coli* cells expressing the desired gene are homogenized, and the supernatant is purified on a column to obtain a desired protein of about 32 kDa or about 40 kDa. For more detailed procedures, reference may be made to Example 3 or 8 described herein later.

The present invention also provides a lipase with a molecular weight of about 40 kDa, which has the ability to recognize both a medium-chain fatty acid and a long-chain fatty acid as substrates and which is produced by a strain belonging to the genus *Tetrasphaera* (preferably belonging to the same species as *Tetrasphaera* sp. strain NITE P-154, more preferably being *Tetrasphaera* sp. strain NITE P-154), or alternatively, a lipase with a molecular weight of about 40 kDa, which can be isolated by a production method comprising the following steps:

applying the culture supernatant of a strain belonging to the genus *Tetrasphaera* onto a hydrophobic resin column to elute the product adsorbed on the hydrophobic resin with a buffer containing 1% nonionic surfactant;

applying the eluate to an anion exchange resin to elute the product adsorbed on the anion exchange resin with a 0.5 M NaCl solution; and applying the eluate, after dialysis, onto an anion exchange column to elute the same with a NaCl gradient solution.

More specifically, the production method comprises steps 1) to 3) shown below:

1) applying the culture supernatant of a strain belonging to the genus *Tetrasphaera* (preferably belonging to the same species as *Tetrasphaera* sp. strain NITE P-154, more preferably being *Tetrasphaera* sp. strain NITE P-154) onto a hydrophobic resin column to elute the product adsorbed on the hydrophobic resin with a buffer containing 1% Triton X-100, if necessary after washing with a buffer containing 0.5% nonionic surfactant (e.g., Triton X-100), etc.;

2) applying the eluate to an anion exchange resin to elute the product adsorbed on the anion exchange resin with a 0.5 M NaCl solution, if necessary after washing with a buffer containing 0.1% amphoteric surfactant (e.g., 3-[(3-Cholamidopropyl)dimethylammonio]-1-propanesulfonate (CHAPS)), etc.; and 3) applying the eluate, after dialysis, onto an anion exchange column to elute the same with a NaCl gradient solution. For example, the dialyzed eluate is applied onto an anion exchange column of 1 ml volume and eluted with a NaCl gradient solution of 0 to 0.75 M. The eluate is fractionated into 0.5 ml volumes.

The above 40 kDa lipase may be isolated and purified in the same manner as described for the 32 kDa lipase from a culture supernatant obtained by culturing a strain belonging to the genus *Tetrasphaera* (preferably belonging to the same species as *Tetrasphaera* sp. strain NITE P-154, more preferably being *Tetrasphaera* sp. strain NITE P-154) in a commercially available medium (see Example 1).

Preferred examples of the above 40 kDa lipase are those having the amino acid sequence shown in SEQ ID NO: 3 and/or SEQ ID NO: 14, more specifically those having the amino acid sequences shown in SEQ ID NOs: 3 and 14.

According to the present invention and the information provided herein, it is possible to obtain the sequence information of a polynucleotide encoding the 40 kDa lipase and such a polynucleotide per se encoding the 40 kDa lipase, for example, by using all or part of the above 40 kDa lipase, the amino acid sequence shown in SEQ ID NO: 3 or SEQ ID NO: 14, a strain belonging to the genus *Tetrasphaera* (preferably belonging to the same species as *Tetrasphaera* sp. strain NITE P-154, more preferably being *Tetrasphaera* sp. strain NITE P-154) or genomic DNA obtained from such a strain, if appropriate in combination with the various procedures disclosed herein for the 32 kDa lipase. More specifically, genomic DNA obtained from a strain belonging to the genus *Tetrasphaera* (preferably belonging to the same species as *Tetrasphaera* sp. strain NITE P-154, more preferably being *Tetrasphaera* sp. strain NITE P-154) is completely digested with an appropriate restriction enzyme(s) and ligated with a cassette corresponding to the restriction enzyme(s) to prepare template DNA. On the other hand, amino acid sequence information obtained from a part of the 40 kDa lipase (e.g., SEQ ID NO: 3 (N-terminal amino acid sequence), SEQ ID NO: 14 (internal amino acid sequence)) is used to design an appropriate primer. PCR is performed using this primer and a cassette primer to obtain a genomic DNA sequence around the 40 kD lipase gene. The nucleotide sequence thus obtained and others may be used to predict the ORF of the gene encoding the 40 kDa lipase. For amplification, cloning and nucleotide sequencing of the predicted ORF and functional confirmation of the encoded protein, it is possible to adapt the procedures described herein which are used for the 32 kDa lipase for the same purposes.

Namely, the present invention also provides a method for producing the nucleotide sequence information of a polynucleotide encoding a 40 kDa lipase, which comprises using the amino acid sequence shown in SEQ ID NO: 3 or SEQ ID NO: 14, all or part of the 40 kDa lipase (i.e., the lipase per se or a fragment thereof) or a strain belonging to the genus *Tetrasphaera* (preferably belonging to the same species as *Tetrasphaera* sp. strain NITE P-154, more preferably being *Tetrasphaera* sp. strain NITE P-154).

II. *Tetrasphaera* sp. Strain NITE P-154

The present invention also provides *Tetrasphaera* sp. strain NITE P-154 capable of producing the lipase of the present invention.

*Tetrasphaera* sp. strain NITE P-154 was selected from a novel marine microorganism library belonging to Marine Biotechnology Institute Co., Ltd. (Japan), depending on whether halo formation occurs on agar plates containing fats of medium-chain fatty acids (MCT).

[Microbiological Properties of *Tetrasphaera* sp. Strain NITE P-154]

*Tetrasphaera* sp. strain NITE P-154 (herein also referred to as "#375") is morphologically seen in coccal form (0.86×0.86 μm) and has no motility. In the physiological aspect, it is Gram-positive and is grown at a temperature ranging from 15° C. to 45° C., and can use D-fructose, D-glucose, D-mannitol, raffinose and sucrose as carbon sources, but cannot use L-arabinose, inositol, L-rhamnose and D-xylose. In the chemotaxonomical aspect, its isoprenoid quinone is MK-8 (H4) and the nucleotide composition of DNA is 70.5%.

TABLE 1

| | |
|---|---|
| a. Morphological properties | |
| 1) Cell shape and size: | coccal, 0.86 × 0.86 μm |
| 2) Presence or absence of motility: | absence |
| b. Culture properties | |
| 1) ISP medium No. 2 plate culture: | forming round, hemispherical, entire and glossy white colonies |
| 2) ISP medium No. 4 plate culture: | forming round, hemispherical, entire and glossy white colonies |
| 3) ISP medium No. 5 plate culture: | forming white colonies with less growth |
| 4) ISP medium No. 6 plate culture: | forming round, hemispherical, entire and glossy yellowish-white colonies |
| 5) ISP medium No. 7 plate culture: | forming white colonies with less growth |
| 6) Marine Agar plate culture: | forming round, hemispherical, entire and glossy white colonies |
| c. Physiological properties | |
| 1) Gram staining: | positive |
| 2) Growth temperature range: | 15-45° C. |
| 3) Alkaline phosphatase activity: | negative |
| 4) Esterase (C4) activity: | positive |
| 5) Esterase lipase (C8) activity: | positive |
| 6) Lipase (C4) activity: | positive |
| 7) Leucine arylamidase activity: | positive |
| 8) Valine arylamidase activity: | positive |
| 9) Cystine arylamidase activity: | negative |
| 10) Trypsin activity: | negative |
| 11) Chymotrypsin activity: | negative |
| 12) Acid phosophatase activity: | positive |
| 13) Naphthol-AS-BI-phosphohydrolase activity: | positive |
| 14) α-Galactosidase activity: | negative |
| 15) β-Galactosidase activity: | positive |
| 16) β-Glucuronidase activity: | negative |
| 17) α-Glucosidase activity: | positive |
| 18) β-Glucosidase activity: | positive |
| 19) N-Acetyl-β-glucosaminidase activity: | negative |
| 20) α-Mannosidase activity: | negative |
| 21) α-Fucosidase activity: | negative |
| 22) Assimilation of carbon sources | |
| L-Arabinose: | − |
| D-Fructose: | + |
| D-Glucose: | + |
| Inositol: | − |
| D-Mannitol: | + |
| L-Rhamnose: | − |
| Raffinose: | + |
| Sucrose: | + |
| D-Xylose: | − |
| using BiOLOG SFP2 microplates | |
| d. Chemotaxonomical properties | |
| 1) Isoprenoid quinine: | MK-8(H4) |
| 2) Nucleotide composition of DNA: | 70.5% |

When cultured in Marine broth 2216 (Difco), *Tetrasphaera* sp. strain NITE P-154 secretes the lipase of the present invention into the extracellular environment.

The present invention also provides a strain or a mutant thereof, which has the same microbiological properties as *Tetrasphaera* sp. strain NITE P-154, as well as a strain or a mutant thereof, which has a 16S rRNA gene consisting of a nucleotide sequence sharing high identity (e.g., more than 98% identity, preferably 98.5% identity, more preferably 99% identity, even more preferably 99.5% identity) with the 16S rRNA gene of *Tetrasphaera* sp. strain NITE P-154 (SEQ ID NO: 1). According to the studies made by the inventors of the present invention, the highest identity was 98% with known strains.

The strain of the present invention and a mutant strain thereof can be used for production of the protein and lipase of the present invention.

The present invention also provides a polynucleotide consisting of the nucleotide sequence shown in SEQ ID NO: 1.

BRIEF DESCRIPTION OF THE DRAWINGS

FIG. 1 shows the nucleotide sequence of the 16S rRNA gene of *Tetrasphaera* sp. NITE P-154 (#375) (SEQ ID NO: 1).

FIG. 3 shows the alignment results between *Streptomyces* sp. putative secretion protein (SEQ ID NO: 37) and *Streptomyces rimosus*-derived GDSL-lipase (SEQ ID NO: 38). The N-terminal 15 amino acid residues of the 32 kDa protein produced by Strain #375 were found to share high identity with a putative secretion protein from relatively closely related *Streptomyces* spp., while this *Streptomyces* sp. putative secretion protein was found to share identity with the amino acid sequences of several lipases including *Streptomyces rimosus*-derived GDSL-lipase.

FIG. 4 shows an amino acid sequence (SEQ ID NO: 11) corresponding to the nucleotide sequence (SEQ ID NO: 10) of a gene expected to encode the 32 kDa protein (lip32 gene). The lip32 gene is composed of at least 777 by and appears to encode a protein composed of 259 amino acid residues.

FIG. 5 shows the construction of a LIP32 protein expression vector (pET22b::lip32Nc).

FIG. 8 shows the nucleotide sequence (SEQ ID NO: 15) of genomic DNA containing a gene encoding LIP32, along with the amino acid sequence of LIP32 (SEQ ID NO: 16). The shaded part represents a sequence identical to the N-terminal amino acid sequence of purified LIP32.

FIG. 9 shows putative pre- and pro-sequences of LIP32, as well as pETLIP32-F, pETLIP32-M and pETLIP32-S vectors.

FIG. 10 shows the nucleotide sequence (SEQ ID NO: 28) of genomic DNA containing a gene encoding LIP40, along with the amino acid sequence of LIP40 (SEQ ID NO: 29). The underlined part represents a secretion signal sequence, while the shaded parts each represent a sequence identical to a partial amino acid sequence of purified LIP40. The double-underlined part represents a conserved region among lipases.

FIG. 11 shows the construction of a LIP40 protein expression vector (pETLIP40HP). '6-His' disclosed as SEQ ID NO: 36.

FIG. 16 shows the amino acid sequence of the mature LIP40 protein (SEQ ID NO:

PREFERRED MODE FOR CARRYING OUT THE INVENTION

Figure 2:
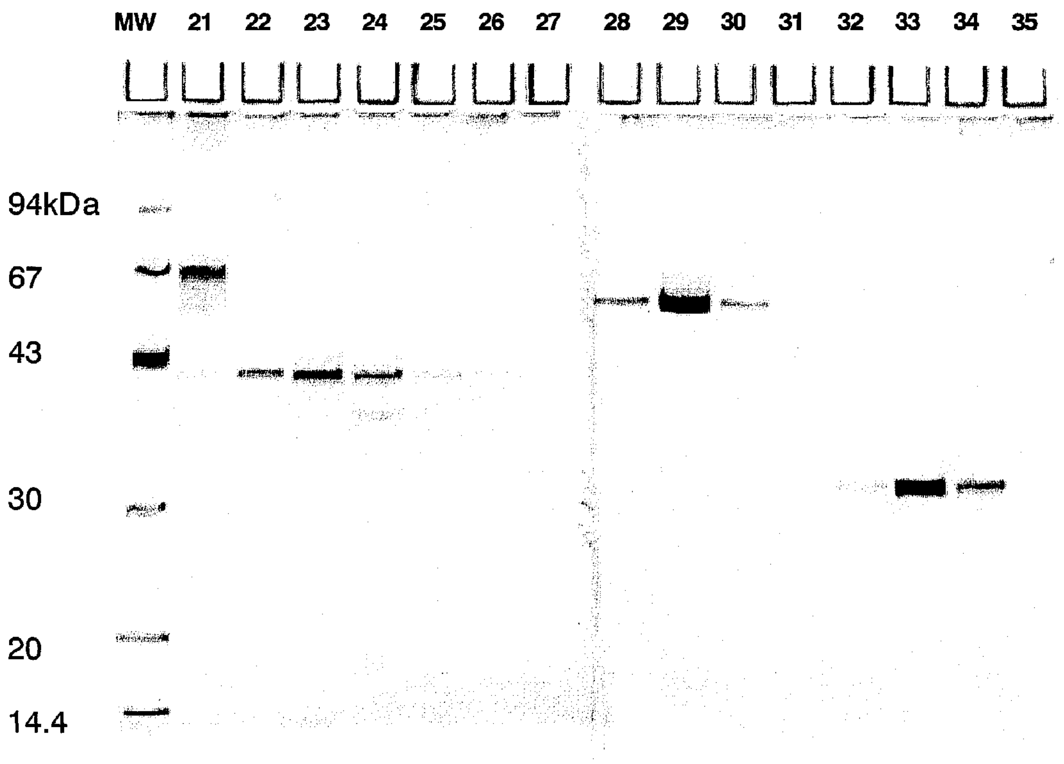
FIG. 2 is a photograph showing SDS-PAGE of each fraction fractionated by HPLC. MW represents a molecular weight marker, while 21 to 35 represent lanes in which fractions #21 to #35 were electrophoresed, respectively.

The 32 kDa or 40 kDa lipase of the present invention can be immobilized on an appropriate carrier for use as an immobilized enzyme.

As a carrier, any conventional resin used for the same purpose may be used, including basic resins (e.g., MARATHON WBA (Dow Chemical), resins of SA series, WA series or FP series (Mitsubishi Chemical Corporation, Japan), and Amberlite IRA series (Organo)), as well as hydrophobic resins (e.g., FPHA (Diaion, Mitsubishi Chemical Corporation, Japan), HP series (Mitsubishi Chemical Corporation, Japan), and Amberlite XAD7 (Organo)).

Likewise, any conventional technique used for the same purpose may be used to immobilize the lipase onto a carrier. For example, relative to 1 part of the above resin carrier, 10 parts of #375 culture supernatant may be added and then directly dried in vacuo, or alternatively, may be adsorbed to remove the supernatant before drying.

Such an immobilized lipase is industrially useful. Namely, when filled into a column, the immobilized enzyme allows a continuous reaction in which source materials are passed through the column. Moreover, the immobilized enzyme can be readily removed from the reaction solution for reuse.

The lipase or immobilized lipase of the present invention can be used in the transfer reaction of a medium-chain fatty acid and/or a long-chain fatty acid, as well as in the production of a medium-chain fatty acid ester and/or a long-chain fatty acid ester. Such an ester encompasses esters of carotenoids (including carotenes and xanthophylls) such as astaxanthin with fatty acids, and esters of polyphenols such as catechin with fatty acids.

As used herein, the term "transfer reaction" is intended to mean esterification or transesterification, unless otherwise specified.

Transfer reaction is useful in producing various fatty acid esters. For example, as in the case of conventional lipases used in industrial practice such as transesterification between triglycerides, production of sterol esters, and production of fatty acid methyl esters, the lipase of the present invention can also be used in these instances. Among esters which can be produced by the lipase of the present invention, the following can be presented as particularly useful examples: sterol esters (e.g., (β-sitosterol caprylic acid ester), astaxanthin caprylic acid ester, catechin caprylic acid ester, etc.

The present invention also provides the sequence information and a part thereof shown in SEQ ID NO: 1, SEQ ID NO: 3, SEQ ID NO: 14, SEQ ID NO: 10, SEQ ID NO: 11, SEQ ID NO: 15, SEQ ID NO: 16, SEQ ID NO: 28 or SEQ ID NO: 29, which has not been provided until the present invention, as well as use of the sequence information and a part thereof.

EXAMPLES

The present invention will now be described in more detail by way of the following examples, which are not intended to limit the scope of the invention.

Example 1

Isolation and Purification of Lipase Proteins from Strain #375 Culture Supernatant, as Well as Sequencing of their N-Terminal 15 Residues Into Marine broth 2216 (Difco) liquid medium, Strain #375 was inoculated at 1% and cultured with shaking at 25° C. for 4 days. The culture supernatant (200 ml) was adsorbed onto a hydrophobic resin Phenyl Sepharose CL4B (2 ml, Amersham Biosciences), which had been equilibrated with Buffer A (50 mM Tris-HCl buffer (pH 8.0)/2 mM $CaCl_2$/2 mM $MgCl_2$), and then subjected to column chromatography. After washing with Buffer A, the column was washed with 10 ml of Buffer A containing 0.5% Triton X-100 to remove substances other than lipase proteins, and then eluted with 10 ml of Buffer A containing 1% Triton X-100 to obtain a lipase active fraction.

This lipase fraction (10 ml) was diluted with 10 volumes of Buffer A and then adsorbed onto an anion exchange resin Q-Sepharose (0.4 ml, Amersham Biosciences). The resin was fully washed with Buffer A containing 0.1% CHAPS to replace the surfactant Triton X-100 with CHAPS, followed by stepwise elution with 0.5 M and 1 M NaCl. The 0.5 M NaCl-eluted fraction (2 ml) showing lipase activity was fully dialyzed against Buffer A containing 0.1% CHAPS, and then eluted by HPLC on an anion exchange column HiTrapQ (1 ml, Amersham Biosciences) with a NaCl gradient of 0 to 0.75 M. The eluate was fractionated into 0.5 ml volumes. The factions were each tested for their lipase activity and analyzed by SDS-PAGE to detect bands. Table 2 shows lipase activity and transfer activity, while FIG. 2 shows the results of SDS-PAGE.

Lipase activity was measured using MU-C8 or MU-C18 as a substrate in the same manner as detailed in Example 3 below, and expressed as "Unit" (1 Unit (1 MU)=the ability of 1 L sample to release 1 μmol MU for 1 minute through hydrolysis).

Likewise, transfer activity was measured as follows. To a mixture of 3-phenyl-1-propanol (10 μl) or 1-phenyl-2-propanol (10 μl) and tricaprilin (150 μl), an enzyme solution (100 μl) was added and reacted while vigorously stirring at 45° C. for 3 days. The reaction solution was centrifuged to collect the upper layer (50 μl). Acetonitrile (50 μl) was added to this layer, 10 μl of which was then analyzed by HPLC. Analysis conditions were set as follows: column: Develosil C30-UG-5 (4.6×150 mm) (Nomura chemical, Aichi, Japan); mobile phase: 90% acetonitrile/0.08% TFA; flow rate: 1 ml/minute; and temperature: room temperature. The results were expressed as formation rate of individual caprylic acid esters.

TABLE 2

| | Lipase activity | | | | | | | | | | | | | | |
|---|---|---|---|---|---|---|---|---|---|---|---|---|---|---|---|
| | Q Fr22 | Q Fr23 | Q Fr24 | Q Fr25 | Q Fr26 | Q Fr27 | Q Fr28 | Q Fr29 | Q Fr30 | Q Fr31 | Q Fr32 | Q Fr33 | Q Fr34 | Q Fr35 | Q Fr36 |
| C8 | 48.50 | 64.75 | 49.24 | 33.62 | 16.49 | 9.95 | 6.07 | 3.94 | 2.97 | 2.47 | 7.78 | 33.97 | 13.94 | 2.69 | 2.17 |
| C18 | 10.67 | 13.46 | 10.58 | 7.58 | 4.73 | 2.88 | 1.70 | 1.24 | 0.90 | 0.76 | 0.74 | 0.69 | 0.57 | 0.46 | 0.43 |
| 3P1 | 15.15 | 22.31 | 20.89 | 13.47 | 5.85 | 3.09 | 2.44 | 2.62 | + | + | + | + | + | + | + |
| 1P2 | 6.24 | 8.28 | 8.57 | 3.97 | + | + | + | + | + | 0.00 | 0.00 | 0.00 | 0.00 | 0.00 | 0.00 |

Two lipases (32 kDa, 40 kDa) were sequenced with a protein sequencer to determine the amino acid sequences of their N-terminal 15 residues. The results obtained are shown in Table 3 and the Sequence Listing (SEQ ID NO: 2, SEQ ID NO: 3).

TABLE 3

Table 3. N-terminal amino acid sequences of lipases (SEQ ID NOS 2-3, respectively, in order of appearance)

| | 1 5 10 15 |
|---|---|
| Lip32k | G D A P A Y E R Y V A L G D s |
| Lip40k | G P D S V P G T A G A T T V T |

With respect to the lipase with a molecular weight of 40 kDa, the corresponding band was further excised from SDS-PAGE and digested with trypsin, followed by reversed-phase HPLC to separate fragment peptides. The 12-residue amino acid sequence LSTNVGPTHLGG (SEQ ID NO: 14) was determined from the N-terminal end of a peptide at any peak.

Example 2

Cloning of 32 kDa Lipase Gene

[Preparation of DNA and RNA from #375]

For preparation of genomic DNA (gDNA) and total RNA from this strain, a DNeasy Tissue Kit (QIAGEN) and an RNeasy Plant isolation Kit (QIAGEN) were used, respectively, according to the protocol of each kit. Reverse transcription (1st strand cDNA synthesis) using the total RNA as a template was accomplished by using SuperScript II Reverse Transcriptase (Invitrogen) according to its protocol.

For ligation of a PCR product into a vector, a TOPO TA-cloning Kit (Invitrogen) was used, and the vector was then transformed into *E. coli* cells in a standard manner. The nucleotide sequence of the cloned DNA fragment was determined by primer walking using primers designed outside the MCS of the cloning vector (e.g., M13 primer M4, RV) or primers designed on known sequences. Sequencing samples were prepared with ABI PRISM BigDye Terminator v3.1 (Applied Biosystems) according to its protocol. The sequencer used was an ABI PRISM 3100-Avant Genetic Analyser (Applied Biosystems), and the data analysis software used was Vector-NTI 9.0 (InforMax).

[Obtaining of Lip32 Gene]

To obtain a gene expected to encode a 32 kDa protein of Strain #375 (hereinafter referred to as the lip32 gene), the sequence of N-terminal 15 amino acid residues of this protein (GDAPAYERYVALGDS (SEQ ID NO: 2)) was searched by blastp against the genebank amino acid sequence database. As a result, high identity was observed with a putative secretion protein from *Streptomyces* spp. (Accession No. CAC42140) which were relatively closely related to Strain #375. This *Streptomyces* sp. putative secretion protein was found to share identity with some amino acid sequences including lipases. Among them, *Streptomyces rimosus*-derived GDSL-lipase (Accession No. AAK84028) was aligned by ClustalW with this putative protein, and the results obtained are shown in FIG. 3. Among sequences conserved between these proteins, two underlined sequences VALGDSYS (SEQ ID NO: 4) and IGGNDS (SEQ ID NO: 5) were used to design a sense degenerate primer 375-dg-F3 (5'-TGGCCCTCGGCGACTCSTAC-'3) (SEQ ID NO: 6) and an antisense degenerate primer 375-dg-R3 (5'-CGTCGTTGCCNCCGATG-3') (SEQ ID NO: 7). Strain #375 cDNA was used as a template to perform DNA amplification by PCR with the primers 375-dg-F3 and 375-dg-R3 using ExTaq (Takara Bio Inc., Japan) under the following conditions: 98° C. for 2 minutes, (98° C. for 20 seconds, 55° C. for 30 seconds, 72° C. for 1 minute)x35 cycles, and 72° C. for 5 minutes. The nucleotide sequence was determined for the resulting DNA fragment to obtain a partial nucleotide sequence covering nucleotides 73-290 of SEQ ID NO: 10. Next, primers 375-IPC32-F1 (5'-CGGCGCGGACACGACGGACATGACG-3') (SEQ ID NO: 8) and 375-IPC32-R1 (5'-GGTAGCAGCCGCCCGCGATGTCGAG-3') (SEQ ID NO: 9) were designed in the outward direction on the resulting sequence. Strain #375 gDNA was digested with a restriction enzyme PstI or NotI and then cyclized by self-ligation. This was used as a template to perform PCR (inverse PCR) with the primers 375-IPC32-F1 and 375-IPC32-R1 using LATaq (Takara Bio Inc., Japan) under the following conditions: 98° C. for 20 seconds, 68° C. for 15 minutes (+10 seconds/cycle)x35 cycles, whereby a neighboring sequence was amplified. The resulting DNA fragment was cloned to determine its partial nucleotide sequence. Taken together with the partial nucleotide sequence obtained earlier, a nucleotide sequence of about 900 by in total was determined for the lip32 region gDNA. The amino acid sequence of LIP32 protein was deduced from the N-terminal amino acid sequence determined in Example 1 (SEQ ID NO: 2). The DNA sequence and deduced amino acid sequence of the lip32 gene region in this strain are shown in FIG. 4 and the Sequence Listing (SEQ ID NO: 10, SEQ ID NO: 11). The N-terminal amino acid sequence determined in Example 1 (SEQ ID NO: 2) was identical to the N-terminal amino acid sequence shown in FIG. 4. In view of these results, the mature LIP32 protein appeared to be a protein composed of 259 amino acid residues.

Moreover, the deduced LIP32 protein was analyzed by ClustalW to determine its identity with known lipase protein amino acid sequences. Table 4 shows identity with the amino acid sequence of each protein.

TABLE 4

| Alignment analysis on LIP32 | | | | | | |
|---|---|---|---|---|---|---|
| | *Streptomyces rimosus* GDSL-ipase | *Candida cylindracea* lipase 1 | *Geo. candidum* GCL1 (LIP1) | *Geo. candidum* GCL2 (LIP2) | *Pseudomonas* sp. lipase | *Rhizopus niveus* lipase |
| #375 LIP32 | 27.5 | 16.3 | 13.4 | 14.4 | 21.4 | 14.5 |

Example 3

Introduction of 32 kDa Lipase Gene into *E. coli* Cells and Lipase Activity

[Preparation of LIP32 Protein (LIP32PH) by *E. coli* Expression System]

For use in *E. coli* expression systems, the cDNA sequence of the Strain #375 lip32 gene ORF was amplified by RT-PCR with primers lip32-Nc-F (5'-CCATGGGCGACGCACCG-GCATACGAACGC-3') (SEQ ID NO: 12) and lip32-Xh-R1 (5'-CTCGAGGGTGAGCTCGTCGATGAGCAGGTG-3') (SEQ ID NO: 13), followed by cloning and sequencing to conform its nucleotide sequence. The cloned cDNA fragment was extracted by digestion with restriction enzymes Nco I and Xho I, and then integrated between recognition sites for these restriction enzymes in an *E. coli* protein expression vector pET22b(+) (Novagen). The resulting vector was designated as pET22b::lip32Nc vector (FIG. 5). *E. coli* strain BL21 (DE3) was transformed with the pET22b::lip32Nc vector and used for protein expression.

Figure 6:
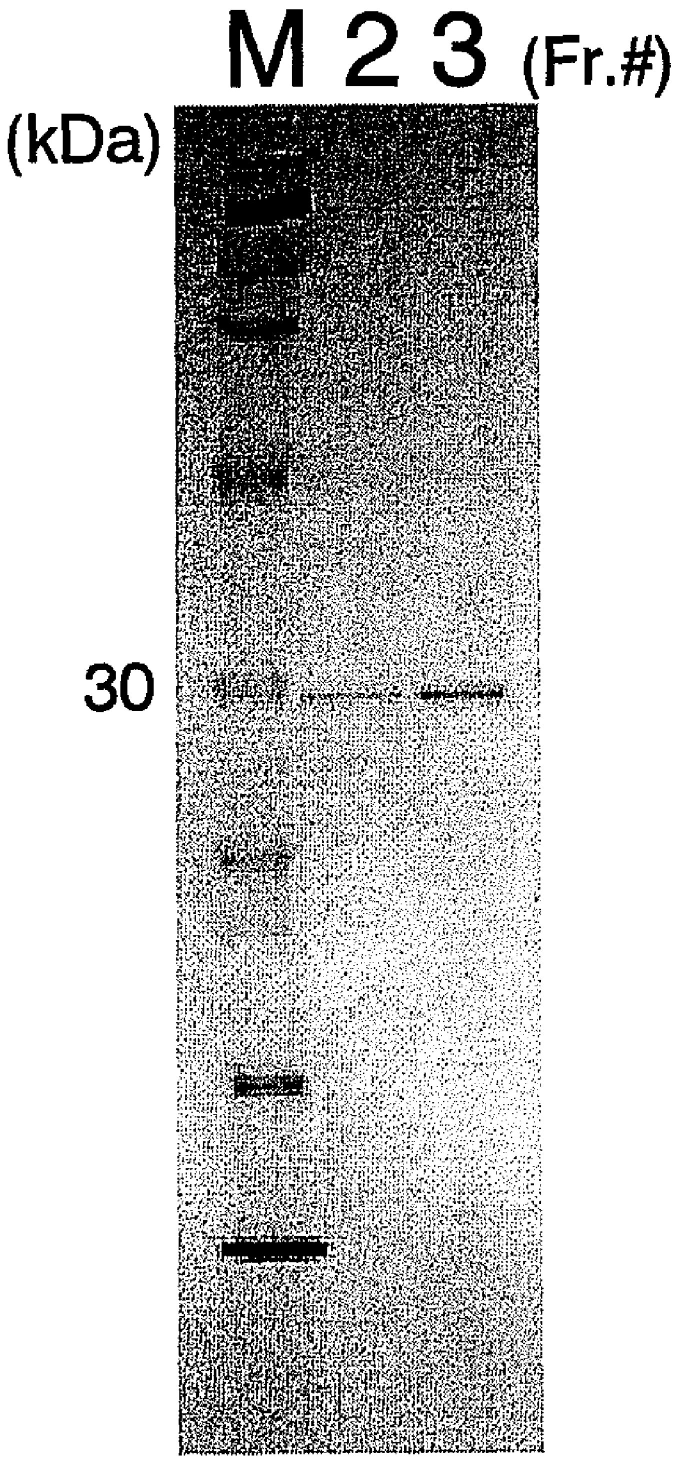
FIG. 6 is a photograph showing SDS-PAGE of the column-purified LIP32 protein. M represents a marker, while 2 and 3 represent lanes in which fractions #2 and #3 were electrophoresed, respectively.
Figure 7:
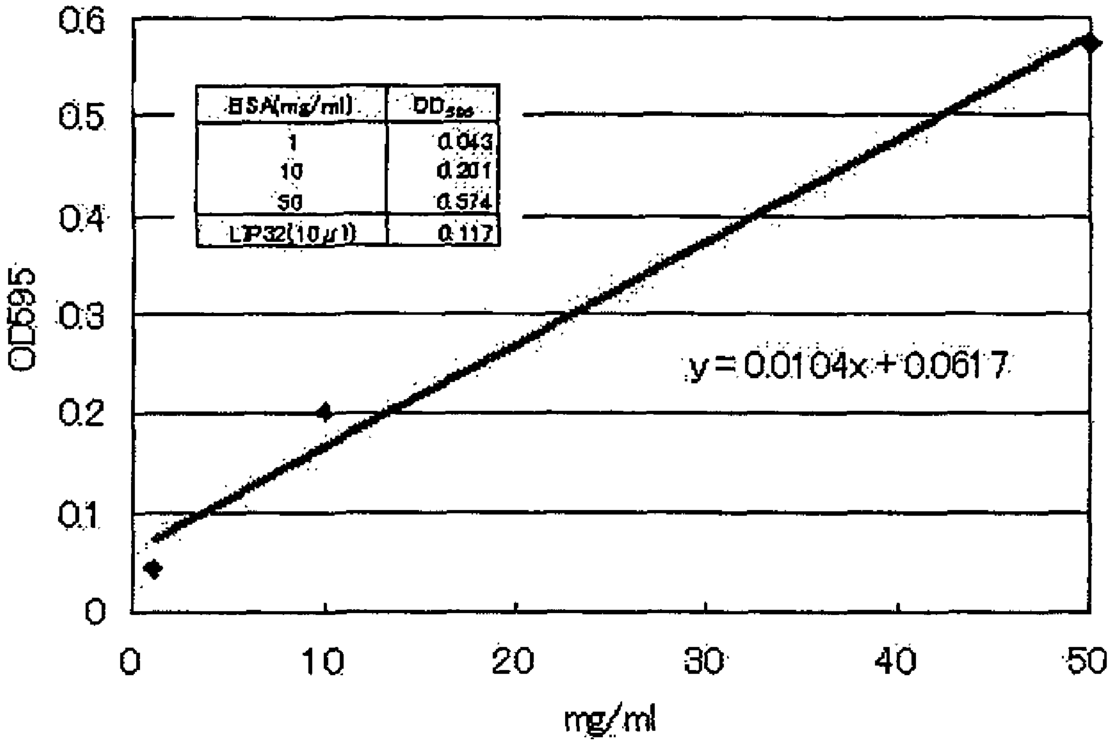
FIG. 7 is a graph showing the Bradford assay results of the column-purified LIP32 protein.

A single colony of *E. coli* cells transformed with the LIP32 protein expression vector (pET22b::lip32Nc) was inoculated into 2 ml LB medium (supplemented with 100 μg/ml ampicillin) and pre-cultured (>150 rpm, 12 hr, 37° C.). The pre-cultured cell suspension was inoculated into 50 ml Enriched medium (2% trypton, 1% yeast extract, 0.5% NaCl, 0.2% (v/v) glycerol, 50 mM $KH_2PO_4$, pH 7.2; supplemented with 100 μg/ml ampicillin) and cultured with shaking (150 rpm, 25° C.). At the time point when the cell suspension reached $OD_{600}$=0.6, isopropyl-β-D-thiogalactopyranoside (IPTG) was added at a final concentration of 1.0 mM to induce LIP32 protein expression. The cells were further cultured with shaking (150 rpm, up to 4 hr, 25° C.) to produce a large amount of LIP32 protein. The *E. coli* cells were collected by centrifugation (6000 rpm, 10 min, 4° C.) and washed twice with Storage buffer (20 mM β-mercaptoethanol (β-ME), 50 mM Tris-HCl, pH 8.0). After being suspended again in 40 ml of ice-cold Lysis buffer (500 mM NaCl, 5 mM imidazole, 20 mM β-ME, 10% (v/v) glycerol, 25 mM Tris-HCl, pH 8.0), the cells were homogenized ultrasonically. The homogenate was centrifuged (10000 rpm, 60 min, 4° C.) and then passed through a filter of pore size ϕ0.22 μm to remove cell debris and insolubles. The resulting solution was used as a crud protein extract. The crud protein extract (10 ml) was passed through a HiTrap Chelating HP column (1.0 ml bed volume) which had been loaded with 1.0 ml of 0.1 M $NiSO_4$ and equilibrated with 10 ml of Equilibration buffer (500 mM NaCl, 20 mM (3-ME, 10% (v/v) glycerol, 25 mM Tris-HCl, pH 8.0). To remove proteins non-specifically bound to the column, the column was washed by sequentially passing 10 ml Wash-1 buffer (500 mM NaCl, 0.8 mM imidazole, 20 mM n-ME, 10% (v/v) glycerol, 25 mM Tris-HCl, pH 8.0) and 1.0 ml Wash-2 buffer (500 mM NaCl, 40 mM imidazole, 20 mM (3-ME, 10% (v/v) glycerol, 25 mM Tris-HCl, pH 8.0). The LIP32 protein was eluted from the column with 5 ml Elution buffer (500 mM NaCl, 250 mM imidazole, 20 mM β-ME, 10% (v/v) glycerol, 25 mM Tris-HCl, pH 8.0), and the eluate was fractionated into 500 μl volumes. The purity and concentration of the protein contained in each fraction were confirmed by SDS-PAGE (FIG. 6) and Bradford assay (FIG. 7). As a result of SDS-PAGE, a band of about 30 kDa corresponding to the LIP32 protein was clearly observed in fractions #2 and #3. Moreover, each fraction was measured for its lipase activity using MU-C8 as a substrate (in the same manner as used in lipase activity measurement described below). As a result, fraction #3 was found to have strong lipase activity. Thus, fraction #3 was used as an enzyme solution of LIP32 protein (about 530 ng/μl) in the subsequent studies.

[Lipase Activity of LIP32 Protein (LIP32PH)]

To determine the lipase activity of LIP32 protein, 20 μl of a diluted *E. coli* culture solution (suspension) and 180 μl of a substrate solution (0.1 mM MU-C8, 50 mM potassium phosphate buffer (pH 7.0), 1% DMF) were mixed to prepare a reaction solution (200 μl), followed by measuring changes in fluorescence intensity at 37° C. for 20 minutes with SPECTRAmax GEMINI XS (Molecular Devices). 1 Unit (1 MU) was defined to be the ability of 1 L sample to release 1 μmol MU for 1 minute through hydrolysis.

Lipase activity was measured by using an *E. coli* suspension induced to express LIP32 protein, indicating that LIP32 had high lipase activity (high ability to hydrolyze MU-C8) (Table 5).

TABLE 5

| Table 5. Lipase activity of LIP32-expressing *E. coli* suspensions | |
|---|---|
| proteins | MU(uM/min/I) MU-C8 |
| 1 ug/ml of OF | 250.52 |
| pET22b(+) | 1.75 |
| pET22b(+)::LiP32 Nc | 54358.00 |

OF: *Candida rugosa*-derived lipase

Example 4

Immobilization of Strain #375 Culture Supernatant onto Anion Exchange Resin and Transfer Activity To 500 mg of a strong anion exchange resin (MARATHON WBA, Dow Chemical), a #375 culture solution (5 ml) was added and dried in vacuo at room temperature to obtain an immobilized enzyme. The immobilized enzyme (50 mg) was added to a mixture of 3-phenyl-1-propanol (25 μl) and tricaprilin (375 μl), and further supplemented with water (20 μl), followed by stirring at 40° C. for 3 days. The reaction solution was analyzed by HPLC, indicating that the formation rate was 75% for caprylic acid ester of 3-phenyl-1-propanol.

Example 5

Immobilization of Strain #375 Culture Supernatant onto Hydrophobic Resin and Transfer Activity The same procedure as shown in Example 4 was repeated using 500 mg of FPHA (Diaion, Mitsubishi Chemical Corporation, Japan) to obtain an immobilized enzyme. This immobilized enzyme (50 mg) was used to perform the same reaction as in Example 4. In this case, the ester formation rate was 47%.

Example 6

Determination of Full-Length lip32 Gene Sequence

Strain #375 gDNA was digested with a restriction enzyme PstI or NotI and then cyclized by self-ligation. This was used as a template to perform PCR (inverse PCR) with the primers 375-IPC32-F1 and 375-IPC32-R1 using LATaq (Takara Bio Inc., Japan) under the following conditions: 98° C. for 20 seconds, 68° C. for 15 minutes (+10 seconds/cycle)×35 cycles, whereby a neighboring sequence was amplified. The resulting DNA fragment was cloned to determine its partial nucleotide sequence and then ligated to the nucleotide sequence obtained earlier (SEQ ID NO: 10) to obtain a genomic DNA sequence containing a LIP32-encoding ORF (SEQ ID NO: 15, FIG. 8) and its deduced amino acid sequence (SEQ ID NO: 16, FIG. 8).

Example 7

Studies on Putative Pre- and Pro-Sequences of LIP32 Protein

For amplification of LIP32-F which encodes the full-length amino acid sequence of LIP32 protein, the following primers were synthesized: primers LIP32-Full-Nde-F (5'-CATATGAGCTCGTCACGTCGTACCGTCCGCACC-3') (SEQ ID NO: 17) and LIP32stop-Xho-Rv (5'-CTCGAGTCAGGTGAGCTCGTCGATGAGCAGGTC-3') (SEQ ID NO: 18). Likewise, for amplification of LIP32-M which encodes an amino acid sequence free from the pre-sequence, primers LIP32-Mid-Nco-F (5'-CCATGGCGACCGAGCGGGCGTCGGCGCCCACG-3') (SEQ ID NO: 19) and LIP32stop-Xho-Rv were synthesized, while for amplification of LIP32-S which encodes an amino acid sequence free from the pre-pro-sequence, primers LIP32-sht-Nco-F (5'-CCATGGGCGACGCACCGGCATACGAACGCTAT-3') (SEQ ID NO: 20) and LIP32stop-Xho-Rv were synthesized. Using Strain #375 gDNA as a template, PCR was performed with each primer set to amplify a DNA fragment, which was then cloned into a pCR4Blunt-TOPO vector (Invitrogen) and confirmed for its nucleotide sequence. Each lip32 gene fragment was excised with restriction enzymes NdeI & XhoI (LIP32-F) or NcoI & XhoI (LIP32-M, -S) and then integrated between recognition sites for these restriction enzymes in an *E. coli* expression vector pET22b(+) (Novagen). The resulting vectors were designated as pETLIP32-F, pETLIP32-M and pETLIP32-S vectors, respectively (FIG. 9).

Each *E. coli* transformant was cultured with shaking in LB medium until $OD_{600}$ reached about 0.6, followed by addition of IPTG at a final concentration of 1 mM. Shaking culture was continued for an additional 3 hours to induce LIP32 protein expression. These *E. coli* suspensions were measured for their lipase activity as follows.

Namely, 20 μl of a diluted *E. coli* suspension and 180 μl of a substrate solution (0.1 mM MU-C8, 50 mM potassium phosphate buffer (pH 7.0), 1% DMF) were mixed to prepare a reaction solution (200 μl), followed by measuring changes in fluorescence intensity at 37° C. for 20 minutes with SPECTRAmax GEMINI XS (Molecular Devices) to determine lipase activity. 1 Unit (1 MU) was defined to be the ability of 1 L sample to release 1 μmol MU for 1 minute through hydrolysis. The analysis results are shown in the table below.

TABLE 6

Table 6. Lipase activity of LIP32-expressing *E. coli* suspensions

| Proteins | MU (μmol/min/l) MU-C8 |
|---|---|
| pET22b(+) | 0.71 |
| pETLIP32-F | 10.47 |
| pETLIP32-M | 23.54 |
| pETLIP32-S | 173.21 |

This result suggested that cleavage of the putative pre- and pro-sequences was required to allow LIP32 protein to exert its activity.

Example 8

Cloning of lip40 Gene

With respect to the lipase with a molecular weight of 40 kDa, the corresponding band was excised from SDS-PAGE and digested with trypsin, followed by reversed-phase HPLC to separate fragment peptides. In addition to the amino acid sequences obtained earlier (SEQ ID NO: 3, SEQ ID NO: 14), the following partial amino acid sequences were obtained from peptides at any peak.

GPDSVPGTAGATTVT (N-terminal) (SEQ ID NO: 3) see Example 1

LSTNVGPTHLGG (SEQ ID NO: 14) see Example 1

```
GPDSVPGTAGATTVT (N-terminal)      (SEQ ID NO: 3)
see Example 1

LSTNVGPTHLGG                      (SEQ ID NO: 14)
see Example 1

APWFGLGAR                         (SEQ ID NO: 21)

QLAESVTEYE                        (SEQ ID NO: 22)

GYAVAFTDYQ                        (SEQ ID NO: 23)
```

Among the partial amino acid sequences, SEQ ID NO: 23 and amino acids 3-12 of SEQ ID NO: 14 were used to synthesize a sense degenerate primer LIP40-9 and an antisense degenerate primer LIP40-5, respectively:

```
primer LIP40-9
(GGNTAYGCNGTNGCNTTYACNGAYTAYCA); (SEQ ID NO: 24)
and

primer LIP40-5
(CCNCCNARRTGNGTNGGNCCNACRTTNGT). (SEQ ID NO: 25)
```

#375 genomic DNA (100 ng) was used as a template to perform PCR using LA Taq with GC buffer (Takara Bio Inc., Japan) in a total volume of 20 µl by using GC buffer II and by adding the primers LIP40-9 and LIP40-5 (each at a final concentration of 10 mM) and LA Taq (0.2 units), under the following conditions: 94° C. for 1 minute, (94° C. for 30 seconds, 50° C. for 30 seconds, 72° C. for 2 minutes)×40 cycles, and 72° C. for 5 minutes. The PCR products were analyzed by agarose gel electrophoresis, confirming a DNA fragment of approximately 0.7 kb. Then, this fragment was excised from the gel, purified with a GFX kit (Amersham) and cloned with a TOPO-TA cloning kit (Invitrogen). The nucleotide sequence was determined for the cloned DNA to obtain a partial nucleotide sequence (covering nucleotides 932-1571 of SEQ ID NO: 28). Next, for full-length cloning of the lip40 gene, inverse PCR was performed. #375 genomic DNA was completely digested with a restriction enzyme NotI and then self-ligated. This was used as a template to perform PCR with primers LIP40-13 (gacgcggttcatgtaggtgtgcgtcc) (SEQ ID NO: 26) and LIP40-14 (gtgcgccaagggcgccaacgtc-cgcc) (SEQ ID NO: 27) using LA Taq with GC buffer (Takara Bio Inc., Japan).

The resulting 7 kb DNA fragment was cloned with a TOPO-TA cloning Kit (Invitrogen) to determine its nucleotide sequence from both ends. The resulting nucleotide sequence was ligated to the nucleotide sequence obtained earlier to obtain the nucleotide sequence of SEQ ID NO: 28. In view of ORF analysis and partial amino acid sequences of LIP40, LIP40 appeared to be encoded by an ORF located between 414 and 1688 bp. This ORF was found to encode a protein composed of 424 amino acid residues (SEQ ID NO: 29, LIP40 amino acid. sequence). The N-terminal amino acid sequence (SEQ ID NO: 3) of the purified protein was identical to the sequence downstream of amino acid 29 in SEQ ID NO: 29 (LIP40 amino acid sequence), so that a peptide composed of amino acids 1-28 of SEQ ID NO: 29 appeared to be a secretion signal (FIG. 10).

The LIP40 amino acid sequence was found to share 72.9% identity with a *Janibacter* sp. HTCC2649-derived hypothetical protein (gi#84498087).

Example 9

Introduction of 40 kDa Lipase Gene into *E. coli* Cells and Lipase Activity

[Preparation of LIP40 Protein by *E. coli* Expression System]

#375 genomic DNA was used as a template to perform PCR with primer L40EcoRI-F1 (GAATTCGGGACCG-GACTCCGTGCCCGGCAC) (SEQ ID NO: 30) or L40NdeI-F3 (CATATGACGTCAGCACTGCTCCGAC-GAGCCCTCGC) (SEQ ID NO: 31) and primer L40HindIII-R1 (AAGCTTCTAGACGGCCCAGCAGTTGCTGAG) (SEQ ID NO: 32) using LA Taq with GC buffer. The amplified DNA fragments of approximately 1.2 kbp were each cloned with a TOPO-TA cloning Kit and confirmed for their nucleotide sequences to obtain plasmids pCR-375LIP40P and pCR-375LIP40S. The plasmid pCR-375LIP40P was digested with EcoRI and HindIII, while the plasmid pCR-375LIP40S was digested with NdeI and HindIII. Then, the resulting fragments were each ligated to an EcoRI- and HindIII-digested or NdeI- and HindIII-digested *E. coli* expression vector pET22b(+) (Novagen) using ligation high (Toyobo Co., Ltd., Japan) to thereby obtain plasmids pET375L40P and pET375LP40S.

A single colony of *E. coli* cells transformed with the LIP40 protein expression vector (plasmid pET375L40P or pET375L40S) was inoculated into 2 ml LB medium supplemented with 100 µg/ml ampicillin and pre-cultured (>150 rpm, 12 hr, 37° C.). The pre-cultured cell suspension was inoculated into 50 ml Enriched medium (2% trypton, 1% yeast extract, 0.5% NaCl, 0.2% (v/v) glycerol, 50 mM $KH_2PO_4$, pH 7.2) supplemented with 100 µg/ml ampicillin and cultured with shaking (150 rpm, 25° C.). At the time point when the cell suspension reached $OD_{600}$=0.6, isopropyl-β-D-thiogalactopyranoside (IPTG) was added at a final concentration of 1.0 mM to induce LIP40 protein expression. The cells were further cultured with shaking (150 rpm, up to 4 hr, 25° C.).

[Lipase Activity of LIP40]

To determine lipase activity, 20 µl of a diluted *E. coli* culture solution (suspension) and 180 µl of a substrate solution (0.1 mM MU-C8 or MU-C18, 50 mM potassium phosphate buffer (pH 7.0), 1% DMF) were mixed to prepare a reaction solution (200 µl), followed by measuring changes in fluorescence intensity at 37° C. for 20 minutes with SPECTRAmax GEMINI XS (Molecular Devices). 1 Unit (1 MU) was defined to be the ability of 1 L sample to release 1 µmol MU for 1 minute through hydrolysis.

The results obtained are shown in the table below.

TABLE 7

Table 7. Lipase activity of *E. coli* culture solutions

| | MU/L (µmol/min/l) | |
|---|---|---|
| | C8 | C18 |
| pET22b(+) | 0.15 | 0 |
| pET375L40S | 191.02 | 23.14 |
| pET375L40P | 5255.73 | 151.06 |

Transfer activity was measured as follows. To a mixture of 3-phenyl-1-propanol (10 µl) or 1-phenyl-2-propanol (10 µl) and tricaprilin (150 µl), an *E. coli* culture solution (100 µl) was added and reacted while vigorously stirring at 45° C. for 3 days. The reaction solution was centrifuged to collect the upper layer (50 µl). Acetonitrile (50 µl) was added to this layer, 10 µl of which was then analyzed by HPLC. Analysis conditions were set as follows: column: Develosil C30-UG-5 (4.6×150 mm) (Nomura chemical, Aichi, Japan); mobile phase: 90% acetonitrile/0.8% TFA; flow rate: 1 ml/minute; and temperature: room temperature. The results were expressed as formation rate of individual caprylic acid esters.

The results obtained are shown in the table below.

TABLE 8

Table 8. Transfer activity of *E. coli* culture solutions

| | 1P2 | 3P1 |
|---|---|---|
| pET22b(+) | — | — |
| pET375L40S | 13.86 | 47.54 |
| pET375L40P | 33.84 | 79.14 |

Example 10

Preparation of LIP40 Protein (LIP40HP) by *E. coli* Expression System

To express a 6-His-tagged (SEQ ID NO: 36) Strain #375 LIP40 protein in *E. coli* cells, a vector was constructed as follows. Strain MBI375 genomic DNA was used as a template to perform amplification by PCR with primers 375L40EcoRI-His-F (5'-GAATTCGCACCACCACCACCACCACGGACCGGACTCCGTGCCCGGCAC-3') (SEQ ID NO: 33) and 375L40HindIII-R1 (5'-AAGCTTCTAGACGGCCCAGCAGTTGCTGAG-3') (SEQ ID NO: 34). The amplified fragment was cloned into a pCR2.1TOPO vector, confirmed for its nucleotide sequence, and then extracted by digestion with restriction enzymes EcoRI and HindIII. The Lip40 gene fragment thus extracted was integrated between recognition sites for these restriction enzymes in an *E. coli* expression vector pET22b(+) (Novagen). The resulting vector was designated as pETLIP40HP vector (FIG. 11). *E. coli* strain BL21 (DE3) was transformed with the pETLIP40HP vector and used for protein expression.

The same procedure as used for the LIP32 protein was repeated to express a LIP40HP protein in *E. coli* cells, except that the culture period after IPTG induction was changed to 12 hours. The LIP40HP protein was purified by affinity purification through the 6-His-tag (SEQ ID NO: 36) fused to the N-terminal end. The procedure used was the same as shown in Example 3 for the LIP32 protein, with the following minor modifications: (1) Lysis buffer, Equilibration buffer and Wash-1 buffer were each replaced with a common buffer (500 mM NaCl, 5 mM imidazole, 2 mM $CaCl_2$, 2 mM $MgCl_2$, 25 mM Tris-HCl, pH 8.0); and (2) Elution buffer was replaced with 500 mM NaCl, 250 mM imidazole, 2 mM $CaCl_2$, 2 mM $MgCl_2$, 25 mM Tris-HCl, pH 8.0.

Example 11

Characterization of LIP32PH and LIP40HP

[Optimum Temperatures for LIP32PH and LIP40HP]

Reaction was initiated by mixing 20 μl of a diluted enzyme solution purified from *E. coli* cells with 180 μl of a substrate solution (0.1 mM MU-C8, 1% DMF, 50 mM Tris-HCl, pH 7.0) which had been maintained at a test temperature (10, 20, 25, 30, 35, 40, 45, 50 or 60° C.). For activity determination, changes in the intensity of MU fluorescence were measured over time during reaction at each test temperature.

Figure 12:
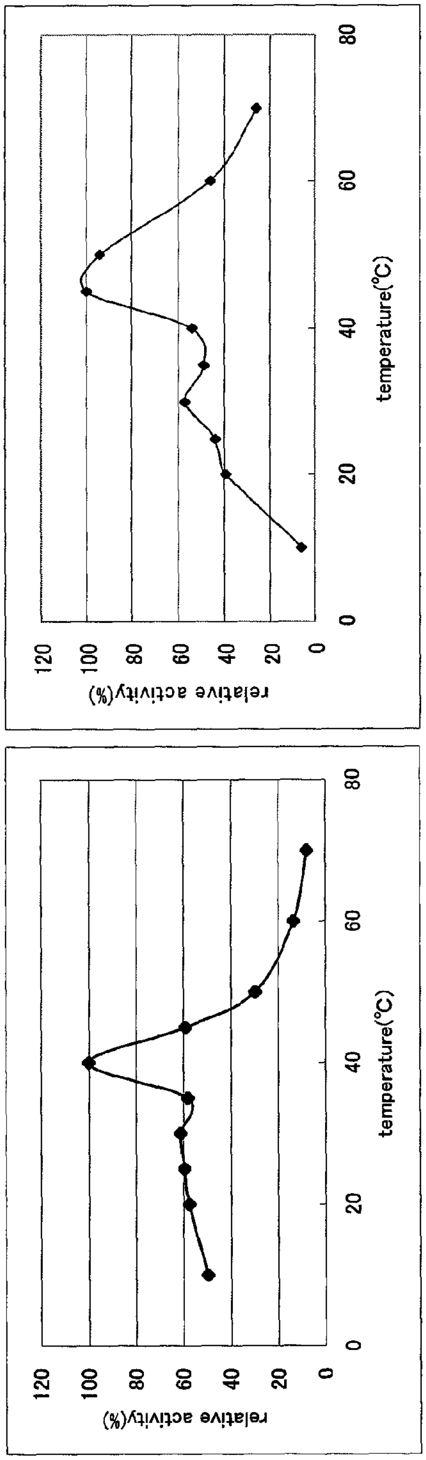
FIG. 12 is graphs showing the optimum temperatures for LIP32PH and LIP40HP.

The results of activity measurement indicated that LIP32PH (obtained in Example 3) had an optimum temperature of 40° C., while LIP40HP had an optimum temperature of 45° C. to 50° C. (FIG. 12).

[Optimum pH for LIP32PH and LIP40HP]

Reaction was initiated by mixing 20 μl of a diluted enzyme solution purified from *E. coli* cells with 180 μl of a substrate solution (0.1 mM MU-C8, 1% DMF, 50 mM buffer of different pH values) which had been maintained at 37° C. For activity determination, the intensity of MU fluorescence was measured over time during reaction at 37° C. for 20 minutes. The following buffers of different pH values were used: 50 mM Sodium acetate-acetic acid (pH 4.0-6.0), 50 mM MES—NaOH (pH 5.5-7.0) and 50 mM Tris-HCl (pH 6.5-9.0).

Figure 13:
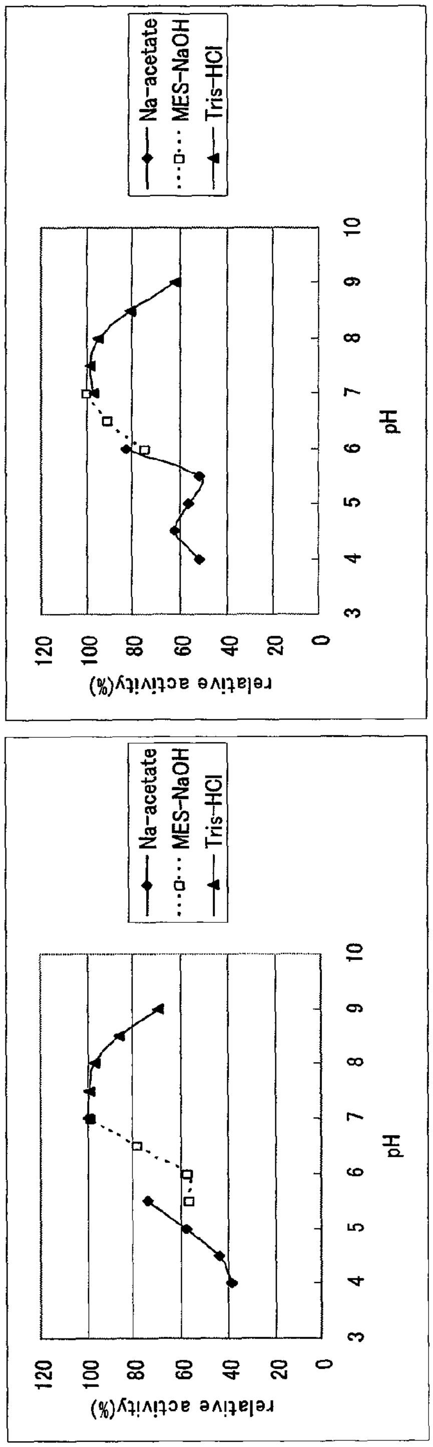
FIG. 13 is graphs showing the optimum pH for LIP32PH and LIP40HP.

The results of activity measurement indicated that LIP32PH and LIP40HP each had an optimum pH of around 7.0 (FIG. 13).

Example 12

Immobilized LIP40HP Enzyme-Catalyzed Fatty Acid Transfer Reaction to Astaxanthin For LIP40HP-catalyzed fatty acid transfer reaction from tricaprilin (MCT) to astaxanthin, an immobilized LIP40HP enzyme was used. The immobilized LIP40HP enzyme (WBA-LIP40HP) was prepared as follows. To 50 mg of a strong anion exchange resin (MARATHON WBA, Dow Chemical), 500 μl of LIP40HP (about 3.65 ng/μl) was added and stirred for 2 hours (1000 rpm, 10° C.), followed by vacuum drying at room temperature.

Figure 14:
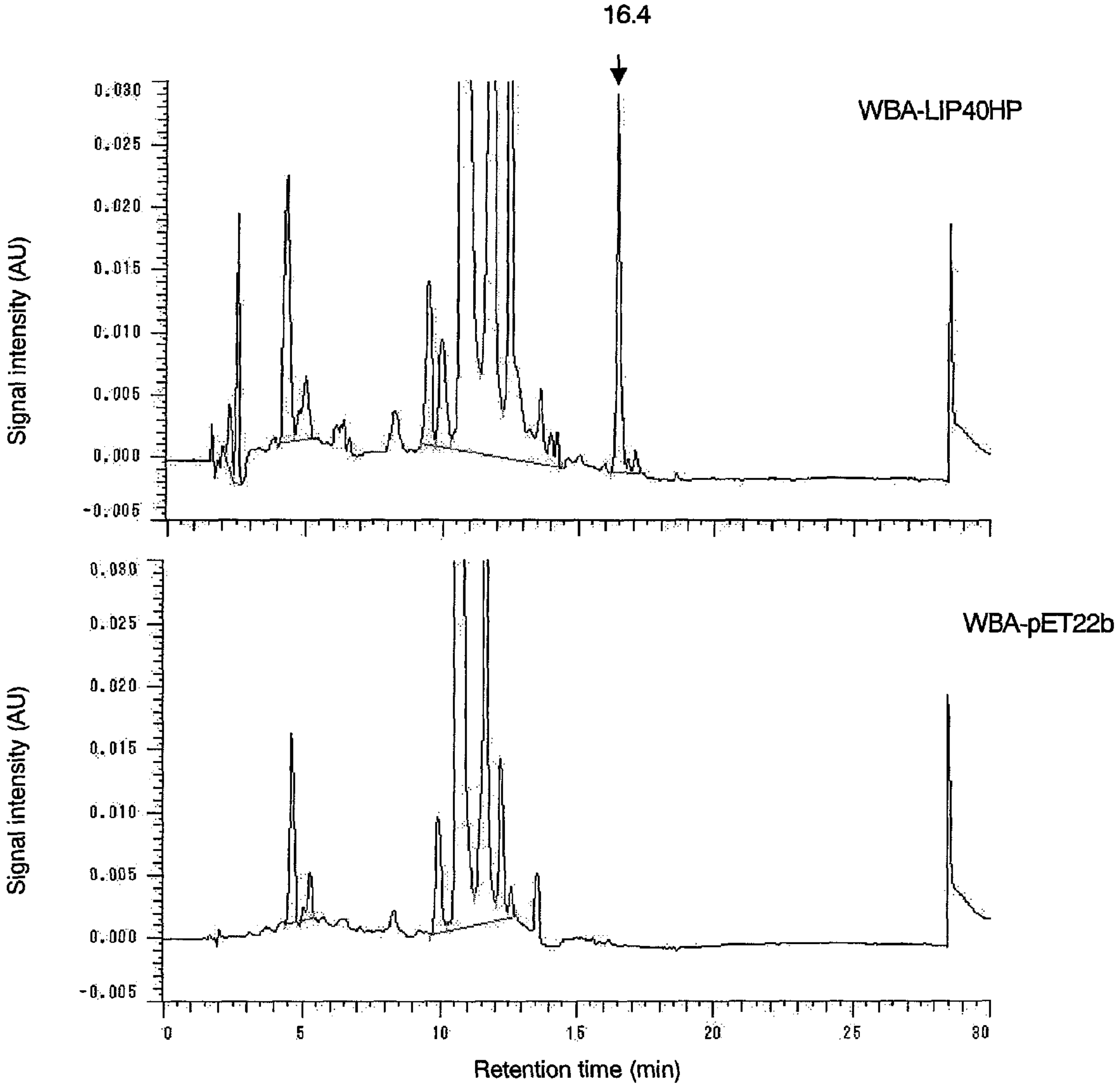
FIG. 14 shows HPLC analysis charts of the reaction solution when using immobilized LIP40HP or a control (pET22b) to effect fatty acid transfer to astaxanthin.

The transfer reaction was performed by sequentially adding WBA-LIP40HP (50 mg) and $H_2O$ (6.25 μl) to a mixture of astaxanthin (1.25 mg, Wako Pure Chemical Industries, Ltd., Japan) and MCT (125 μl), and then allowing the mixture to stand at 45° C. for 3 days. To the reaction solution, 100 μl acetone was added and stirred, followed by centrifugation to collect the upper layer (100 μl), 20 μl of which was then analyzed by HPLC. Analysis conditions were set as follows: column: Develosil C30-UG-5 (Nomura Chemical Co., Ltd., Japan, 4.6×150 mm); mobile phase: 75%-100% acetone, gradient elution for 1-15 minutes at a flow rate of 1.0 ml/min; analysis temperature: room temperature; and detection wavelength: 480 nm. Transfer activity was determined as formation rate of astaxanthin ester at a retention time of 16.4 minutes. The analysis indicated that the formation rate was 2.25% for caprylic acid ester of astaxanthin (FIG. 14). On the other hand, there was no formation of caprylic acid ester for astaxanthin during reaction using WBA-pET22b prepared as a control in the same manner (FIG. 14).

Example 13

LIP40HP-Catalyzed Fatty Acid Transfer Reaction to Catechin

Figure 15:
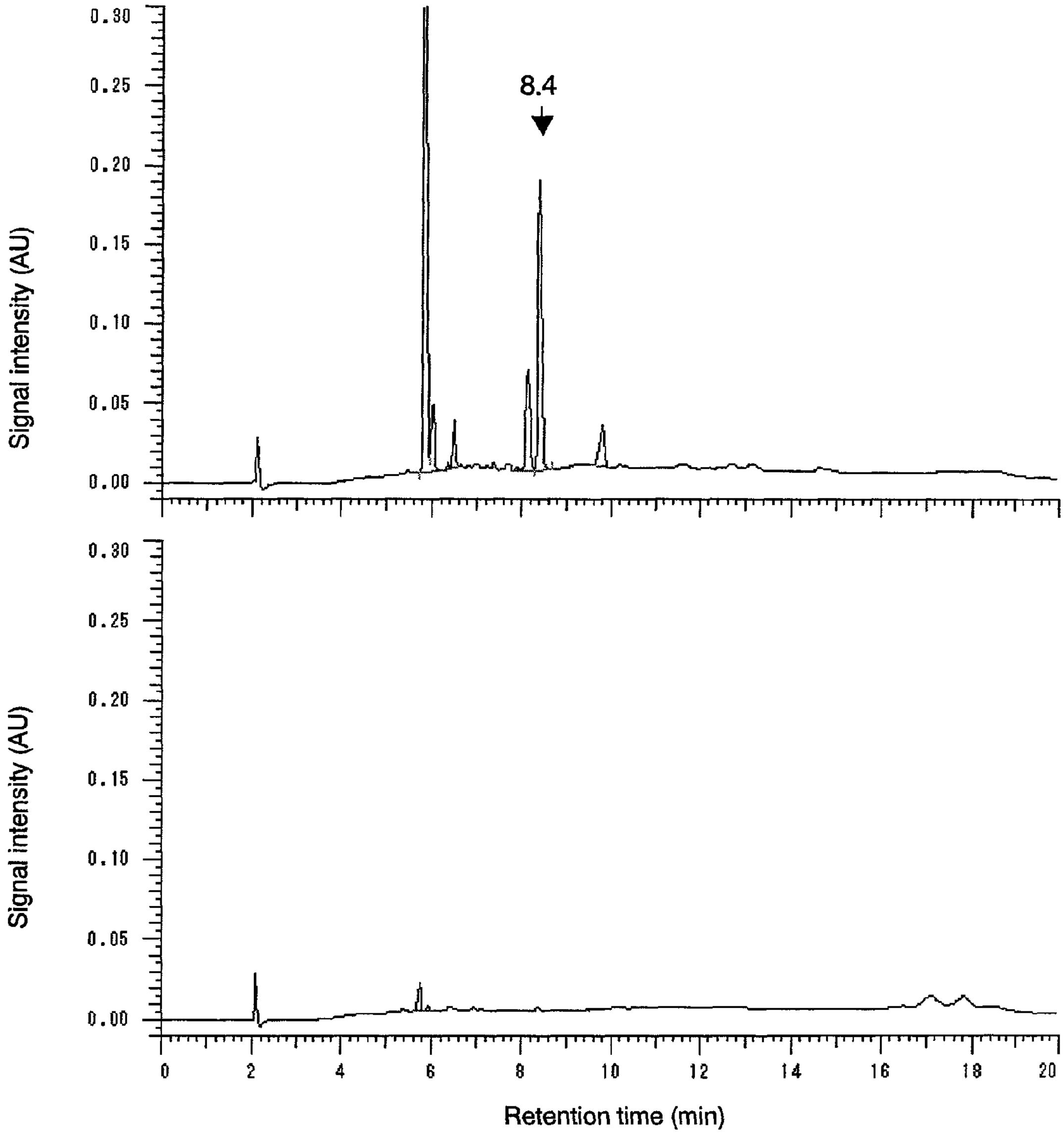
FIG. 15 shows HPLC analysis charts of the reaction solution when using LIP40HP or a control (pET22b) to effect fatty acid transfer to catechin.

LIP40-catalyzed fatty acid transfer reaction from tricaprilin (MCT) to catechin was performed by adding 50 μl LIP40HP enzyme solution (1.0 μg/μl) to a mixture of 100 μl catechin solution (0.01 mg/μl) and 150 μl MCT, followed by stirring at 45° C. for 2 days. The reaction solution was centrifuged to collect the oil layer, and an equal volume of acetonitrile was added thereto, 10 μl of which was then analyzed by HPLC. Analysis conditions were set as follows: column: Develosil C30-UG-5 (Nomura Chemical Co., Ltd., Japan, 4.6×150 mm), mobile phase: (A) 0.1% TFA and (B) 90% acetonitrile/0.08% TFA under gradient conditions of 5% to 100% Eluent B/5 minutes at a flow rate of 1.0 ml/min; analysis temperature: room temperature; and detection wavelength: 280 nm. Transfer activity was determined as formation rate of catechin ester at a retention time of 8.4 minutes. The analysis indicated that the formation rate was 38.70% for caprylic acid ester of catechin (FIG. 15). On the other hand, there was no formation of caprylic acid ester for catechin during reaction using pET22b prepared as a control in the same manner (FIG. 15).

The invention claimed is:

1. An isolated polynucleotide comprising ($A_1$), ($B_1$), ($C_1$), ($D_1$), ($E_1$), ($F_1$) or ($G_1$) shown below:

($A_1$) an isolated polynucleotide which consists of all of the nucleotide sequence shown in SEQ ID NO: 10 or a part thereof covering at least nucleotides 25-801;

($B_1$) an isolated polynucleotide which is hybridizable under stringent conditions with a polynucleotide consisting of a nucleotide sequence complementary to the nucleotide sequence of the polynucleotide shown in ($A_1$) and which encodes a protein having lipase activity;

($C_1$) an isolated polynucleotide which consists of a nucleotide sequence comprising substitution, deletion, insertion and/or addition of 1 to 9 nucleotides in the nucleotide sequence of the polynucleotide shown in ($A_1$) and which encodes a protein having lipase activity;

($D_1$) an isolated polynucleotide which shares an identity of at least 80% or more with the nucleotide sequence of the polynucleotide shown in ($A_1$) and which encodes a protein having lipase activity;

($E_1$) an isolated polynucleotide which encodes a protein consisting of the amino acid sequence shown in SEQ ID NO: 11;

($F_1$) an isolated polynucleotide which encodes a protein consisting of an amino acid sequence comprising substitution, deletion, insertion and/or addition of 1 to 9 amino acids in the amino acid sequence shown in SEQ ID NO: 11 and having lipase activity; or ($G_1$) an isolated polynucleotide which encodes a protein consisting of an amino acid sequence sharing an identity of at least 80% or more with the amino acid sequence shown in SEQ ID NO: 11 and having lipase activity, wherein the stringent condition consists of hybridization at 65° C. in a solution containing 6 M urea, 0.4% sodium dodecyl sulfate (SDS), and 0.1×saline sodium citrate (SSC).

2. The isolated polynucleotide according to claim 1, which is selected from ($A_1$'), ($B_1$'), ($C_1$'), ($D_1$'), ($E_1$'), ($F_1$') or ($G_1$') shown below:

($A_1$') an isolated polynucleotide which consists of all of the nucleotide sequence shown in SEQ ID NO: 10 or a part thereof covering nucleotides 25-801;

($B_1$') an isolated polynucleotide which is hybridizable under stringent conditions with a polynucleotide consisting of a nucleotide sequence complementary to the nucleotide sequence of the polynucleotide shown in ($A_1$') and which encodes a protein having lipase activity;

($C_1$') an isolated polynucleotide which consists of a nucleotide sequence comprising substitution, deletion, insertion and/or addition of 1 to 9 nucleotides in the nucleotide sequence of the polynucleotide shown in ($A_1$') and which encodes a protein having lipase activity;

($D_1$') an isolated polynucleotide which shares an identity of at least 80% or more with the nucleotide sequence of the polynucleotide shown in ($A_1$') and which encodes a protein having lipase activity;

($E_1$') an isolated polynucleotide which encodes a protein consisting of the amino acid sequence shown in SEQ ID NO: 11;

($F_1$') an isolated polynucleotide which encodes a protein consisting of an amino acid sequence comprising substitution, deletion, insertion and/or addition of 1 to 9 amino acids in the amino acid sequence shown in SEQ ID NO: 11 and having lipase activity; or ($G_1$') an isolated polynucleotide which encodes a protein consisting of an amino acid sequence sharing an identity of at least 80% or more with the amino acid sequence shown in SEQ ID NO: 11 and having lipase activity wherein the stringent condition consists of hybridization at 65° C. in a solution containing 6 M urea, 0.4% sodium dodecyl sulfate (SDS), and 0.1×saline sodium citrate (SSC).

3. The isolated polynucleotide according to claim 1, which comprises ($A_2$), ($B_2$), ($C_2$), ($D_2$), ($E_2$), ($F_2$) or ($G_2$) shown below:

($A_2$) an isolated polynucleotide which consists of all of the nucleotide sequence shown in SEQ ID NO: 15 or a part thereof covering at least nucleotides 247-1167 or 388-1164;

($B_2$) an isolated polynucleotide which is hybridizable under stringent conditions with a polynucleotide consisting of a nucleotide sequence complementary to the nucleotide sequence of the polynucleotide shown in ($A_2$) and which encodes a protein having lipase activity;

($C_2$) an isolated polynucleotide which consists of a nucleotide sequence comprising substitution, deletion, insertion and/or addition of 1 to 9 nucleotides in the nucleotide sequence of the polynucleotide shown in ($A_2$) and which encodes a protein having lipase activity;

($D_2$) an isolated polynucleotide which shares an identity of at least 80% or more with the nucleotide sequence of the polynucleotide shown in ($A_2$) and which encodes a protein having lipase activity;

($E_2$) an isolated polynucleotide which encodes a protein consisting of all of the amino acid sequence shown in SEQ ID NO: 16 or a part thereof covering at least amino acids 48-306;

($F_2$) an isolated polynucleotide which encodes a protein consisting of an amino acid sequence comprising substitution, deletion, insertion and/or addition of 1 to 9 amino acids in the amino acid sequence of the protein shown in ($E_2$) and having lipase activity; or ($G_2$) an isolated polynucleotide which encodes a protein consisting of an amino acid sequence sharing an identity of at least 80% or more with the amino acid sequence of the protein shown in ($E_2$) and having lipase activity wherein the stringent condition consists of hybridization at 65° C. in a solution containing 6 M urea, 0.4% sodium dodecyl sulfate (SDS), and 0.1×saline sodium citrate (SSC).

4. The isolated polynucleotide according to claim 3, which is selected from ($A_2$'), ($B_2$'), ($C_2$'), ($D_2$'), ($E_2$'), ($F_2$') or ($G_2$') shown below:

($A_2$') an isolated polynucleotide which consists of all of the nucleotide sequence shown in SEQ ID NO: 15 or a part thereof covering nucleotides 247-1167 or 388-1164;

($B_2$') an isolated polynucleotide which is hybridizable under stringent conditions with a polynucleotide consisting of a nucleotide sequence complementary to the nucleotide sequence of the polynucleotide shown in ($A_2$') and which encodes a protein having lipase activity;

($C_2$') an isolated polynucleotide which consists of a nucleotide sequence comprising substitution, deletion, insertion and/or addition of 1 to 9 nucleotides in the nucleotide sequence of the polynucleotide shown in ($A_2$') and which encodes a protein having lipase activity;

($D_2$') an isolated polynucleotide which shares an identity of at least 80% or more with the nucleotide sequence of the polynucleotide shown in ($A_2$') and which encodes a protein having lipase activity;

($E_2$') an isolated polynucleotide which encodes a protein consisting of all of the amino acid sequence shown in SEQ ID NO: 16 or a part thereof covering at least amino acids 48-306;

($F_2$') an isolated polynucleotide which encodes a protein consisting of an amino acid sequence comprising substitution, deletion, insertion and/or addition of 1 to 9 amino acids in the amino acid sequence of the protein shown in ($E_2$') and having lipase activity; or ($G_2$') an isolated polynucleotide which encodes a protein consisting of an amino acid sequence sharing an identity of at least 80% or more with the amino acid sequence of the protein shown in ($E_2$') and having lipase activity, wherein the stringent condition consists of hybridization at 65° C. in a solution containing 6 M urea, 0.4% sodium dodecyl sulfate (SDS), and 0.1×saline sodium citrate (SSC).

5. The isolated polynucleotide according to claim 1, which is derived from the genus *Tetrasphaera.*

6. A vector carrying the isolated polynucleotide according to claim 1.

7. A transformant transformed with the vector according to claim 6.

8. The isolated polynucleotide according to claim 1, wherein ($D_1$") and ($G_1$") are respectively:

($D_1$") an isolated polynucleotide which shares an identity of at least 90% or more with the nucleotide sequence of the polynucleotide shown in ($A_1$) and which encodes a protein having lipase activity; and ($G_1$") an isolated polynucleotide which encode a protein consisting of an amino acid sequence sharing an identity of at least 90% or more with the amino acid sequence shown in SEQ ID NO: 11 and having lipase activity.

9. The isolated polynucleotide according to claim 1, wherein ($D_1$") and ($G_1$") are respectively:

($D_1$") an isolated polynucleotide which shares an identity of at least 95% or more with the nucleotide sequence of the polynucleotide shown in ($A_1$) and which encodes a protein having lipase activity; and (G") an isolated polynucleotide which encode a protein consisting of an amino acid sequence sharing an identity of at least 95% or more with the amino acid sequence shown in SEQ ID NO: 11 and having lipase activity.

* * * * *

SEQUENCE LISTING

<160> NUMBER OF SEQ ID NOS: 38

<210> SEQ ID NO 1
<211> LENGTH: 1442
<212> TYPE: DNA
<213> ORGANISM: Tetrasphaera sp.

<400> SEQUENCE: 1

```
taacacatgc aagtcgaacg gtgacctcga gagcttgctc tcgagcgatc agtggcgaac      60

gggtgagtaa cacgtgagta acctgcccca gactctggaa taaccccggg aaaccggagc     120

taataccgga tacgagacga agctgcatgg ctatcgtctg gaaagttttt cggtctggga     180

tggactcgcg gcctatcagc ttgttggtga ggtaacggct caccaaggcg acgacgggta     240

gccggcctga gagggcgacc ggccacactg ggactgagac acggcccaga ctcctacggg     300

aggcagcagt ggggaatatt gcacaatggg cgcaagcctg atgcagcgac gccgcgtgag     360

ggatgacggc cttcgggttg taaacctctt tcagcaggga agaagcgaaa gtgacggtac     420

ctgcagaaga agcaccggct aactacgtgc cagcagccgc ggtaatacgt agggtgcgag     480

cgttgtccgg aattattggg cgtaaagagc ttgtaggcgg tttgtcgcgt ctgctgtgaa     540

aatccggggc tcaaccccgg acttgcagtg ggtacgggca gactagagtg tggtagggga     600

gactggaatt cctggtgtag cggtgaaatg cgcagatatc aggaggaaca ccgatggcga     660

aggcaggtct ctgggccact actgacgctg agaagcgaaa gcatggggag cgaacaggat     720

tagataccct ggtagtccat gccgtaaacg ttgggcgcta ggtgtgggac tcattccacg     780

agttccgtgc cgcagctaac gcattaagcg ccccgcctgg ggagtacggc cgcaaggcta     840

aaactcaaag gaattgacgg gggcccgcac aagcggcgga gcatgtggat taattcgatg     900

caacgcgaag aaccttacca aggcttgaca tataccggaa acacctggag acaggtgccc     960

cgcaaggtcg gtatacaggt ggtgcatggt tgtcgtcagc tcgtgtcgtg agatgttggg    1020

ttaagtcccg caacgagcgc aaccctcgtt ctatgttgcc agcgcgttat ggcggggact    1080

catagaagac tgccggggtc aactcggagg aaggtgggga tgaggtcaaa tcatcatgcc    1140

ccttatgtct tgggcttcac acatgctaca atggccggta caaagggctg cgaaaccgcg    1200

aggtggagcg aatcccaaaa aaccggtctc agttcggatt ggggtctgca actcgacccc    1260

atgaagttgg agtcgctagt aatcgcagat cagcaacgct gcggtgaata cgttcccggg    1320

ccttgtacac accgcccgtc aagtcacgaa agtcggtaac acccgaagcc ggtggcccaa    1380

cccttgtgga gggagccgtc gaaggtggga ctggcgattg ggactaagtc gtaacaaggt    1440

aa                                                                   1442
```

<210> SEQ ID NO 2
<211> LENGTH: 15
<212> TYPE: PRT
<213> ORGANISM: Tetrasphaera sp.

<400> SEQUENCE: 2

```
Gly Asp Ala Pro Ala Tyr Glu Arg Tyr Val Ala Leu Gly Asp Ser
1               5                   10                  15
```

<210> SEQ ID NO 3
<211> LENGTH: 15
<212> TYPE: PRT
<213> ORGANISM: Tetrasphaera sp.

-continued

<400> SEQUENCE: 3

Gly Pro Asp Ser Val Pro Gly Thr Ala Gly Ala Thr Thr Val Thr
1               5                   10                  15

<210> SEQ ID NO 4
<211> LENGTH: 8
<212> TYPE: PRT
<213> ORGANISM: Streptomyces rimosus

<400> SEQUENCE: 4

Val Ala Leu Gly Asp Ser Tyr Ser
1               5

<210> SEQ ID NO 5
<211> LENGTH: 6
<212> TYPE: PRT
<213> ORGANISM: Streptomyces rimosus

<400> SEQUENCE: 5

Ile Gly Gly Asn Asp Ser
1               5

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggccctcgg cgactcstac                                               20

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, g, t, unknown or other

<400> SEQUENCE: 7
cgtcgttgcc nccgatg                                                  17

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggcgcggac acgacggaca tgacg                                         25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 9

ggtagcagcc gcccgcgatg tcgag                                          25


<210> SEQ ID NO 10
<211> LENGTH: 840
<212> TYPE: DNA
<213> ORGANISM: Tetrasphaera sp.
<220> FEATURE:
<221> NAME/KEY: CDS
<222> LOCATION: (25)..(801)

<400> SEQUENCE: 10

acgcaggccg cgcccgcccc ggac ggc gac gca ccg gca tac gaa cgc tat       51
                           Gly Asp Ala Pro Ala Tyr Glu Arg Tyr
                           1               5

gtc gcc ctc ggc gac tcc tac acg gcg gcg ccg ctc gtg ccg aac ctc      99
Val Ala Leu Gly Asp Ser Tyr Thr Ala Ala Pro Leu Val Pro Asn Leu
10                  15                  20                  25

gac atc gcg ggc ggc tgc tac cgc tcg acg aac aat tac ccg agc ctg     147
Asp Ile Ala Gly Gly Cys Tyr Arg Ser Thr Asn Asn Tyr Pro Ser Leu
                30                  35                  40

ctc gcg cgc gag ctc ggt gtg acg acg ttc gtc gac gcg agc tgc tcc     195
Leu Ala Arg Glu Leu Gly Val Thr Thr Phe Val Asp Ala Ser Cys Ser
            45                  50                  55

ggc gcg gac acg acg gac atg acg cag agc cag ctc gcc ggc gtc gca     243
Gly Ala Asp Thr Thr Asp Met Thr Gln Ser Gln Leu Ala Gly Val Ala
        60                  65                  70

ccg cag ctg gac aac ctc acc ccc gac acc gac ctc gtc acg ctg agc     291
Pro Gln Leu Asp Asn Leu Thr Pro Asp Thr Asp Leu Val Thr Leu Ser
    75                  80                  85

atc ggc ggc aac gac ttc aac gtc ttc ggc acc ctc gtc ggc tat tgc     339
Ile Gly Gly Asn Asp Phe Asn Val Phe Gly Thr Leu Val Gly Tyr Cys
90                  95                  100                 105

acg acg ctg cgg gcg agc gac ccg acg ggc agc ccg tgc cgg gac gag     387
Thr Thr Leu Arg Ala Ser Asp Pro Thr Gly Ser Pro Cys Arg Asp Glu
                110                 115                 120

atg cgc agc gac ggg cag gac cgg ctg ctc gcc gcc gtc aaa gag acc     435
Met Arg Ser Asp Gly Gln Asp Arg Leu Leu Ala Ala Val Lys Glu Thr
            125                 130                 135

cgg gca cgc atc gac gcg gtc atc gcc gag atc gag gag cgc tca ccg     483
Arg Ala Arg Ile Asp Ala Val Ile Ala Glu Ile Glu Glu Arg Ser Pro
        140                 145                 150

gac gcg cgc atc ctc gtc gtc ggg tac ccg cag atc gcg ccg cgt cag     531
Asp Ala Arg Ile Leu Val Val Gly Tyr Pro Gln Ile Ala Pro Arg Gln
    155                 160                 165

ggc acc tgc ccc gac ctg ctg ccg ctc gcc gac ggt gac gtg tcg tat     579
Gly Thr Cys Pro Asp Leu Leu Pro Leu Ala Asp Gly Asp Val Ser Tyr
170                 175                 180                 185

gcc gtg cag gtc aac aag cgc ctc acc gac gcg ctg cgg cag gcg gcc     627
Ala Val Gln Val Asn Lys Arg Leu Thr Asp Ala Leu Arg Gln Ala Ala
                190                 195                 200

aag agc aac caa gtg gag tac gtc gac gtg tgg aag gcg agc cag ggg     675
Lys Ser Asn Gln Val Glu Tyr Val Asp Val Trp Lys Ala Ser Gln Gly
            205                 210                 215

cac gac atc tgc tcc ggc gac ccg tgg gtc aac ggg cag gtc acc gac     723
His Asp Ile Cys Ser Gly Asp Pro Trp Val Asn Gly Gln Val Thr Asp
        220                 225                 230

atc acc cgg gcg cag aac tac cac ccg ttc gcg aac gag cag cgc gcc     771
Ile Thr Arg Ala Gln Asn Tyr His Pro Phe Ala Asn Glu Gln Arg Ala
    235                 240                 245
```

-continued

```
atc gcc gac ctg ctc atc gac gag ctc acc tgaggaccac caccggggca        821
Ile Ala Asp Leu Leu Ile Asp Glu Leu Thr
250                 255

tcacgatgtg cactgccga                                                 840


<210> SEQ ID NO 11
<211> LENGTH: 259
<212> TYPE: PRT
<213> ORGANISM: Tetrasphaera sp.

<400> SEQUENCE: 11

Gly Asp Ala Pro Ala Tyr Glu Arg Tyr Val Ala Leu Gly Asp Ser Tyr
1               5                   10                  15

Thr Ala Ala Pro Leu Val Pro Asn Leu Asp Ile Ala Gly Gly Cys Tyr
            20                  25                  30

Arg Ser Thr Asn Asn Tyr Pro Ser Leu Leu Ala Arg Glu Leu Gly Val
        35                  40                  45

Thr Thr Phe Val Asp Ala Ser Cys Ser Gly Ala Asp Thr Thr Asp Met
    50                  55                  60

Thr Gln Ser Gln Leu Ala Gly Val Ala Pro Gln Leu Asp Asn Leu Thr
65                  70                  75                  80

Pro Asp Thr Asp Leu Val Thr Leu Ser Ile Gly Gly Asn Asp Phe Asn
                85                  90                  95

Val Phe Gly Thr Leu Val Gly Tyr Cys Thr Thr Leu Arg Ala Ser Asp
            100                 105                 110

Pro Thr Gly Ser Pro Cys Arg Asp Glu Met Arg Ser Asp Gly Gln Asp
        115                 120                 125

Arg Leu Leu Ala Ala Val Lys Glu Thr Arg Ala Arg Ile Asp Ala Val
    130                 135                 140

Ile Ala Glu Ile Glu Glu Arg Ser Pro Asp Ala Arg Ile Leu Val Val
145                 150                 155                 160

Gly Tyr Pro Gln Ile Ala Pro Arg Gln Gly Thr Cys Pro Asp Leu Leu
                165                 170                 175

Pro Leu Ala Asp Gly Asp Val Ser Tyr Ala Val Gln Val Asn Lys Arg
            180                 185                 190

Leu Thr Asp Ala Leu Arg Gln Ala Ala Lys Ser Asn Gln Val Glu Tyr
        195                 200                 205

Val Asp Val Trp Lys Ala Ser Gln Gly His Asp Ile Cys Ser Gly Asp
    210                 215                 220

Pro Trp Val Asn Gly Gln Val Thr Asp Ile Thr Arg Ala Gln Asn Tyr
225                 230                 235                 240

His Pro Phe Ala Asn Glu Gln Arg Ala Ile Ala Asp Leu Leu Ile Asp
                245                 250                 255

Glu Leu Thr


<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

ccatgggcga cgcaccggca tacgaacgc                                       29


<210> SEQ ID NO 13
```

-continued

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

ctcgagggtg agctcgtcga tgagcaggtg                                    30


<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ser Thr Asn Val Gly Pro Thr His Leu Gly Gly
1               5                   10


<210> SEQ ID NO 15
<211> LENGTH: 1203
<212> TYPE: DNA
<213> ORGANISM: Tetrasphaera sp.
<220> FEATURE:
<221> NAME/KEY: CDS
<222> LOCATION: (247)..(1164)

<400> SEQUENCE: 15

cgcggttcat cgagcagatg gcacggcggg tcgacgggcg cgtcgtggcg cccgagctcg     60

acgacctcgg cgccgcggtc gtcggcagct atctcgggtc tcggggctcg cgcggtcctg    120

gcggtgggtc ctaccgtgac cacttcgggg acctgttcgg ctcgcggggt ttctgggcgg    180

gctgacccgc acgacggcgc ggcgtatcgt ggcgagggac gcacccgcca tgaagggacc    240

tcacgg atg agc tcg tca cgt cgt acc gtc cgc acc gcc gtc gcc gct      288
       Met Ser Ser Ser Arg Arg Thr Val Arg Thr Ala Val Ala Ala
       1               5                   10

gcg tgg gct gct gcg ctg ctc gtc gcc gtg ccc ggt gcc cag tcg atg      336
Ala Trp Ala Ala Ala Leu Leu Val Ala Val Pro Gly Ala Gln Ser Met
15                  20                  25                  30

gcc gcg acc gag cgg gcg tcg gcg ccc acg cag gcc gcg ccc gcc ccg      384
Ala Ala Thr Glu Arg Ala Ser Ala Pro Thr Gln Ala Ala Pro Ala Pro
                35                  40                  45

gac ggc gac gca ccg gca tac gaa cgc tat gtc gcc ctc ggc gac tcc      432
Asp Gly Asp Ala Pro Ala Tyr Glu Arg Tyr Val Ala Leu Gly Asp Ser
            50                  55                  60

tac acg gcg gcg ccg ctc gtg ccg aac ctc gac atc gcg ggc ggc tgc      480
Tyr Thr Ala Ala Pro Leu Val Pro Asn Leu Asp Ile Ala Gly Gly Cys
        65                  70                  75

tac cgc tcg acg aac aat tac ccg agc ctg ctc gcg cgc gag ctc ggt      528
Tyr Arg Ser Thr Asn Asn Tyr Pro Ser Leu Leu Ala Arg Glu Leu Gly
    80                  85                  90

gtg acg acg ttc gtc gac gcg agc tgc tcc ggc gcg gac acg acg gac      576
Val Thr Thr Phe Val Asp Ala Ser Cys Ser Gly Ala Asp Thr Thr Asp
95                  100                 105                 110

atg acg cag agc cag ctc gcc ggc gtc gca ccg cag ctg gac aac ctc      624
Met Thr Gln Ser Gln Leu Ala Gly Val Ala Pro Gln Leu Asp Asn Leu
                115                 120                 125

acc ccc gac acc gac ctc gtc acg ctg agc atc ggc ggc aac gac ttc      672
Thr Pro Asp Thr Asp Leu Val Thr Leu Ser Ile Gly Gly Asn Asp Phe
            130                 135                 140
```

-continued

```
aac gtc ttc ggc acc ctc gtc ggc tat tgc acg acg ctg cgg gcg agc      720
Asn Val Phe Gly Thr Leu Val Gly Tyr Cys Thr Thr Leu Arg Ala Ser
        145                 150                 155

gac ccg acg ggc agc ccg tgc cgg gac gag atg cgc agc gac ggg cag      768
Asp Pro Thr Gly Ser Pro Cys Arg Asp Glu Met Arg Ser Asp Gly Gln
    160                 165                 170

gac cgg ctg ctc gcc gcc gtc aaa gag acc cgg gca cgc atc gac gcg      816
Asp Arg Leu Leu Ala Ala Val Lys Glu Thr Arg Ala Arg Ile Asp Ala
175                 180                 185                 190

gtc atc gcc gag atc gag gag cgc tca ccg gac gcg cgc atc ctc gtc      864
Val Ile Ala Glu Ile Glu Glu Arg Ser Pro Asp Ala Arg Ile Leu Val
                195                 200                 205

gtc ggg tac ccg cag atc gcg ccg cgt cag ggc acc tgc ccc gac ctg      912
Val Gly Tyr Pro Gln Ile Ala Pro Arg Gln Gly Thr Cys Pro Asp Leu
            210                 215                 220

ctg ccg ctc gcc gac ggt gac gtg tcg tat gcc gtg cag gtc aac aag      960
Leu Pro Leu Ala Asp Gly Asp Val Ser Tyr Ala Val Gln Val Asn Lys
        225                 230                 235

cgc ctc acc gac gcg ctg cgg cag gcg gcc aag agc aac caa gtg gag     1008
Arg Leu Thr Asp Ala Leu Arg Gln Ala Ala Lys Ser Asn Gln Val Glu
    240                 245                 250

tac gtc gac gtg tgg aag gcg agc cag ggg cac gac atc tgc tcc ggc     1056
Tyr Val Asp Val Trp Lys Ala Ser Gln Gly His Asp Ile Cys Ser Gly
255                 260                 265                 270

gac ccg tgg gtc aac ggg cag gtc acc gac atc acc cgg gcg cag aac     1104
Asp Pro Trp Val Asn Gly Gln Val Thr Asp Ile Thr Arg Ala Gln Asn
                275                 280                 285

tac cac ccg ttc gcg aac gag cag cgc gcc atc gcc gac ctg ctc atc     1152
Tyr His Pro Phe Ala Asn Glu Gln Arg Ala Ile Ala Asp Leu Leu Ile
            290                 295                 300

gac gag ctc acc tgaggaccac caccggggca tcacgatgtg cactgccga          1203
Asp Glu Leu Thr
        305


<210> SEQ ID NO 16
<211> LENGTH: 306
<212> TYPE: PRT
<213> ORGANISM: Tetrasphaera sp.

<400> SEQUENCE: 16

Met Ser Ser Ser Arg Arg Thr Val Arg Thr Ala Val Ala Ala Ala Trp
1               5                   10                  15

Ala Ala Ala Leu Leu Val Ala Val Pro Gly Ala Gln Ser Met Ala Ala
            20                  25                  30

Thr Glu Arg Ala Ser Ala Pro Thr Gln Ala Ala Pro Ala Pro Asp Gly
        35                  40                  45

Asp Ala Pro Ala Tyr Glu Arg Tyr Val Ala Leu Gly Asp Ser Tyr Thr
    50                  55                  60

Ala Ala Pro Leu Val Pro Asn Leu Asp Ile Ala Gly Gly Cys Tyr Arg
65                  70                  75                  80

Ser Thr Asn Asn Tyr Pro Ser Leu Leu Ala Arg Glu Leu Gly Val Thr
                85                  90                  95

Thr Phe Val Asp Ala Ser Cys Ser Gly Ala Asp Thr Thr Asp Met Thr
            100                 105                 110

Gln Ser Gln Leu Ala Gly Val Ala Pro Gln Leu Asp Asn Leu Thr Pro
        115                 120                 125

Asp Thr Asp Leu Val Thr Leu Ser Ile Gly Gly Asn Asp Phe Asn Val
    130                 135                 140
```

-continued

```
Phe Gly Thr Leu Val Gly Tyr Cys Thr Thr Leu Arg Ala Ser Asp Pro
145                 150                 155                 160

Thr Gly Ser Pro Cys Arg Asp Glu Met Arg Ser Asp Gly Gln Asp Arg
                165                 170                 175

Leu Leu Ala Ala Val Lys Glu Thr Arg Ala Arg Ile Asp Ala Val Ile
            180                 185                 190

Ala Glu Ile Glu Glu Arg Ser Pro Asp Ala Arg Ile Leu Val Val Gly
        195                 200                 205

Tyr Pro Gln Ile Ala Pro Arg Gln Gly Thr Cys Pro Asp Leu Leu Pro
    210                 215                 220

Leu Ala Asp Gly Asp Val Ser Tyr Ala Val Gln Val Asn Lys Arg Leu
225                 230                 235                 240

Thr Asp Ala Leu Arg Gln Ala Ala Lys Ser Asn Gln Val Glu Tyr Val
                245                 250                 255

Asp Val Trp Lys Ala Ser Gln Gly His Asp Ile Cys Ser Gly Asp Pro
            260                 265                 270

Trp Val Asn Gly Gln Val Thr Asp Ile Thr Arg Ala Gln Asn Tyr His
        275                 280                 285

Pro Phe Ala Asn Glu Gln Arg Ala Ile Ala Asp Leu Leu Ile Asp Glu
    290                 295                 300

Leu Thr
305
```

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
catatgagct cgtcacgtcg taccgtccgc acc 33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ctcgagtcag gtgagctcgt cgatgagcag gtc 33

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ccatggcgac cgagcgggcg tcggcgccca cg 32

<210> SEQ ID NO 20
<211> LENGTH: 32
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 20
ccatgggcga cgcaccggca tacgaacgct at 32

<210> SEQ ID NO 21
<211> LENGTH: 9
<212> TYPE: PRT
<213> ORGANISM: Tetrasphaera sp.

<400> SEQUENCE: 21

Ala Pro Trp Phe Gly Leu Gly Ala Arg
1               5

<210> SEQ ID NO 22
<211> LENGTH: 10
<212> TYPE: PRT
<213> ORGANISM: Tetrasphaera sp.

<400> SEQUENCE: 22

Gln Leu Ala Glu Ser Val Thr Glu Tyr Glu
1               5                   10

<210> SEQ ID NO 23
<211> LENGTH: 10
<212> TYPE: PRT
<213> ORGANISM: Tetrasphaera sp.

<400> SEQUENCE: 23

Gly Tyr Ala Val Ala Phe Thr Asp Tyr Gln
1               5                   10

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other

<400> SEQUENCE: 24
ggntaygcng tngcnttyac ngaytayca 29

<210> SEQ ID NO 25
<211> LENGTH: 29
<212> TYPE: DNA
<213> ORGANISM: Artificial Sequence
<220> FEATURE:

-continued

<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other

<400> SEQUENCE: 25
ccnccnarrt gngtnggncc nacrttngt 29

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacgcggttc atgtaggtgt gcgtcc 26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtgcgccaag ggcgccaacg tccgcc 26

<210> SEQ ID NO 28
<211> LENGTH: 2577
<212> TYPE: DNA
<213> ORGANISM: Tetrasphaera sp.
<220> FEATURE:
<221> NAME/KEY: CDS
<222> LOCATION: (414)..(1685)
<220> FEATURE:
<221> NAME/KEY: modified_base
<222> LOCATION: (990)..(990)
<223> OTHER INFORMATION: a, c, g, t, unknown or other

<400> SEQUENCE: 28
gtgaacagga cgagcccgac ggagagcccg aggatcggga cgcggttggc gcggatgtcg 60
atgagcgagg tgttcagggc cgcggcatag agcagcggcg gcaacagccc gagcaggacg 120

-continued

```
atgtcgggct cgagctcggg gtgcgggatg aacggcaggt acgagccgac gatgcccacg    180

ccgagcagcg cgatgggcga cgggaggccg aacggggcgc acaggcgcgc gacgacgatg    240

acggtcacgg cgatcgcggc gagggtgagg gcgaggtcca ccggcacatt gtccgtcaac    300

ggcggaggcc gtcgcccccg ctccggttgc cgggcagatt acccgcctgt agcgtggaag    360

tggcggcgta tccccagacg ctcgctcgac acccctgcgg aaggtcttcg aca atg       416
                                                            Met
                                                            1

acg tca gca ctg ctc cga cga gcc ctc gcc cct gcc ctc gcc ctc ggt      464
Thr Ser Ala Leu Leu Arg Arg Ala Leu Ala Pro Ala Leu Ala Leu Gly
            5                   10                  15

ctc gcg gtc acc ctc ggc gca ccc gcg tcg gcc gga ccg gac tcc gtg      512
Leu Ala Val Thr Leu Gly Ala Pro Ala Ser Ala Gly Pro Asp Ser Val
        20                  25                  30

ccc ggc acc gcc ggt gcg acg acc gtg acc gac acc ccc gag ccg cct      560
Pro Gly Thr Ala Gly Ala Thr Thr Val Thr Asp Thr Pro Glu Pro Pro
    35                  40                  45

cgc ccc gcg ttc tac gag ccg ccg gcg acg atc ccc ggg aca ccc ggc      608
Arg Pro Ala Phe Tyr Glu Pro Pro Ala Thr Ile Pro Gly Thr Pro Gly
50                  55                  60                  65

acg gtc atc cgc acc gag tcc gcg acc tac ctc ctc gac ccg ctc ggc      656
Thr Val Ile Arg Thr Glu Ser Ala Thr Tyr Leu Leu Asp Pro Leu Gly
                70                  75                  80

ctg tcg cag acc gtc gtg acg tcg acg cgg gtc atg tac tcc tcg ctc      704
Leu Ser Gln Thr Val Val Thr Ser Thr Arg Val Met Tyr Ser Ser Leu
            85                  90                  95

gac cgg cag ggc cgg ccc atc gcc gtc acc ggc acg atc ctc gag ccg      752
Asp Arg Gln Gly Arg Pro Ile Ala Val Thr Gly Thr Ile Leu Glu Pro
        100                 105                 110

aag gcg ccg tgg ttc ggg ctc ggt gcg cga ccg ctc atc tcg tat gcc      800
Lys Ala Pro Trp Phe Gly Leu Gly Ala Arg Pro Leu Ile Ser Tyr Ala
    115                 120                 125

gtg ggc acc cag ggc atg ggt gac cgg tgc gcg ccg tcg cgc cag ctc      848
Val Gly Thr Gln Gly Met Gly Asp Arg Cys Ala Pro Ser Arg Gln Leu
130                 135                 140                 145

gcc gag tcc gtg acc gag tac gaa gcc ggg ttc atc tcc ggg ctc gtc      896
Ala Glu Ser Val Thr Glu Tyr Glu Ala Gly Phe Ile Ser Gly Leu Val
                150                 155                 160

acg cgc ggg tac gcc gtt gcg ttc acc gac tac cag ggt ctc tcg acg      944
Thr Arg Gly Tyr Ala Val Ala Phe Thr Asp Tyr Gln Gly Leu Ser Thr
            165                 170                 175

ccc ggg acg cac acc tac atg aac cgc gtc gtc cag gga cgc gcc ntc      992
Pro Gly Thr His Thr Tyr Met Asn Arg Val Val Gln Gly Arg Ala Xaa
        180                 185                 190

ctc gac atg gca cga gca gcg ctg cgc cgc aac ggg acc acg ctg act     1040
Leu Asp Met Ala Arg Ala Ala Leu Arg Arg Asn Gly Thr Thr Leu Thr
    195                 200                 205

gcg acg act ccg gtg ggg atc tac ggc tac tcg cag ggc ggc ggc gcg     1088
Ala Thr Thr Pro Val Gly Ile Tyr Gly Tyr Ser Gln Gly Gly Gly Ala
210                 215                 220                 225

agt gcg tcg gcg gcc gag ctc acc gcg acc tat gcc ccg gag ctg cgg     1136
Ser Ala Ser Ala Ala Glu Leu Thr Ala Thr Tyr Ala Pro Glu Leu Arg
                230                 235                 240

gtc aag ggt gcc ctc gcc ggt gcg gtt ccg gcg gac ctc aag gcg gtg     1184
Val Lys Gly Ala Leu Ala Gly Ala Val Pro Ala Asp Leu Lys Ala Val
            245                 250                 255

gcc cag aac ctc gat ggc tcg ctg tat gcc gag ttc ctc aac ttc gcg     1232
Ala Gln Asn Leu Asp Gly Ser Leu Tyr Ala Glu Phe Leu Asn Phe Ala
```

-continued

```
        260                 265                 270

ctg ctc ggc ctg tcg gcc ggg tac ggc atc gac ctc aac tcc tac ctc     1280
Leu Leu Gly Leu Ser Ala Gly Tyr Gly Ile Asp Leu Asn Ser Tyr Leu
    275                 280                 285

aac gag cgg ggg cag gcc gtg gcc gcg gac acc gag aac cac tgc gtc     1328
Asn Glu Arg Gly Gln Ala Val Ala Ala Asp Thr Glu Asn His Cys Val
290                 295                 300                 305

acc gac ctg ccg aag gcg gcc ttc cag cag tcg tcg acg ctg acg cgc     1376
Thr Asp Leu Pro Lys Ala Ala Phe Gln Gln Ser Ser Thr Leu Thr Arg
                310                 315                 320

gac ggt cgc ggt ctg ctc gac tac ctc gac gag gag ccg ttc gcg tcg     1424
Asp Gly Arg Gly Leu Leu Asp Tyr Leu Asp Glu Glu Pro Phe Ala Ser
            325                 330                 335

gtc atc gcc gac aac cgc atc ggc acg atc aag ccg tcc gtg ccc gtc     1472
Val Ile Ala Asp Asn Arg Ile Gly Thr Ile Lys Pro Ser Val Pro Val
        340                 345                 350

ctc atc tcg cac tcg gtc gcc gac gac gtc atc ccg tac gcc gtg ggc     1520
Leu Ile Ser His Ser Val Ala Asp Asp Val Ile Pro Tyr Ala Val Gly
    355                 360                 365

aag cag ctc gcc cgc gac tgg tgc gcc aag ggc gcc aac gtc cgc ctc     1568
Lys Gln Leu Ala Arg Asp Trp Cys Ala Lys Gly Ala Asn Val Arg Leu
370                 375                 380                 385

tcg acg aac gtc ggc ccg acc cac ctc ggc ggg gcc ctg ccg tcg gcg     1616
Ser Thr Asn Val Gly Pro Thr His Leu Gly Gly Ala Leu Pro Ser Ala
                390                 395                 400

gcg gag agc tac gcg ttc ttc gag gcg cgc ttc gcc ggc gtg ccc cag     1664
Ala Glu Ser Tyr Ala Phe Phe Glu Ala Arg Phe Ala Gly Val Pro Gln
            405                 410                 415

ctc agc aac tgc tgg gcc gtc tagctgtact cggccgcgag gttggtgaca        1715
Leu Ser Asn Cys Trp Ala Val
        420

cgtaggcgtt gacgacgagg agaacctccg ggtgaggtgt ggattgtcga agtcccaacc   1775

gcccggaggt tctcgtgtcc cacgctaacg ctcgtctgaa tgttcatggt cgtcgtctgt   1835

tggtcgaccg cgttcgccgc caagggtggg cagtggctca tgccgcgaag gcgatgggga   1895

tctcgcgtca gtgcgctcac aggtgggtgt ccaggttcga caccgagggt gaggccgggt   1955

tgtcggaccg gtcctcggcg ccgcactcca gccctcgccg caccgcgaca tcggtcgagg   2015

acgcggtggt ggctgcccgg cgggagcacc ggcgtggtca ggactggatc gggcctgaac   2075

tgggtgtccc ggcacgcacg gtcagccgaa tcctgcgccg ccatgacctg ccctacctgc   2135

ggcattgcga cccgctcacc ggggacgtga tccgcgcctc gaagaccacc gcggtccggt   2195

atgaacgcga ccgccccggc gagctggttc acgttgatgt caagaagatc gggcgcatcc   2255

ccgacggtgg cgggtggaga gcccacggcc gccagatggg ctcgaccgcg gcacggaaga   2315

aagcgcgcat cgggtacgac tacgtgcact ccatggtcga tgaccactcc cggctcgcgt   2375

acagcgagat cctcccggac gagaccggcc ccacctgcgc cgcgttcatc ctgcgcgccg   2435

ccgaacactt cgccgcccac ggcatcgccg ccatcgaacg cgtcatcacc gacaaccact   2495

tcagctaccg caaaagcaac gacgtcaggg acgcgatgac cgccatgggg gccacgcaca   2555

agttcatccg gccccactgc cc                                             2577
```

<210> SEQ ID NO 29
<211> LENGTH: 424
<212> TYPE: PRT
<213> ORGANISM: Tetrasphaera sp.
<220> FEATURE:
<221> NAME/KEY: MOD_RES -continued
<222> LOCATION: (193)..(193)
<223> OTHER INFORMATION: Any amino acid

<400> SEQUENCE: 29

```
Met Thr Ser Ala Leu Leu Arg Arg Ala Leu Ala Pro Ala Leu Ala Leu
1               5                   10                  15

Gly Leu Ala Val Thr Leu Gly Ala Pro Ala Ser Ala Gly Pro Asp Ser
            20                  25                  30

Val Pro Gly Thr Ala Gly Ala Thr Thr Val Thr Asp Thr Pro Glu Pro
        35                  40                  45

Pro Arg Pro Ala Phe Tyr Glu Pro Pro Ala Thr Ile Pro Gly Thr Pro
    50                  55                  60

Gly Thr Val Ile Arg Thr Glu Ser Ala Thr Tyr Leu Leu Asp Pro Leu
65                  70                  75                  80

Gly Leu Ser Gln Thr Val Val Thr Ser Thr Arg Val Met Tyr Ser Ser
                85                  90                  95

Leu Asp Arg Gln Gly Arg Pro Ile Ala Val Thr Gly Thr Ile Leu Glu
            100                 105                 110

Pro Lys Ala Pro Trp Phe Gly Leu Gly Ala Arg Pro Leu Ile Ser Tyr
        115                 120                 125

Ala Val Gly Thr Gln Gly Met Gly Asp Arg Cys Ala Pro Ser Arg Gln
    130                 135                 140

Leu Ala Glu Ser Val Thr Glu Tyr Glu Ala Gly Phe Ile Ser Gly Leu
145                 150                 155                 160

Val Thr Arg Gly Tyr Ala Val Ala Phe Thr Asp Tyr Gln Gly Leu Ser
                165                 170                 175

Thr Pro Gly Thr His Thr Tyr Met Asn Arg Val Val Gln Gly Arg Ala
            180                 185                 190

Xaa Leu Asp Met Ala Arg Ala Ala Leu Arg Arg Asn Gly Thr Thr Leu
        195                 200                 205

Thr Ala Thr Thr Pro Val Gly Ile Tyr Gly Tyr Ser Gln Gly Gly Gly
    210                 215                 220

Ala Ser Ala Ser Ala Ala Glu Leu Thr Ala Thr Tyr Ala Pro Glu Leu
225                 230                 235                 240

Arg Val Lys Gly Ala Leu Ala Gly Ala Val Pro Ala Asp Leu Lys Ala
                245                 250                 255

Val Ala Gln Asn Leu Asp Gly Ser Leu Tyr Ala Glu Phe Leu Asn Phe
            260                 265                 270

Ala Leu Leu Gly Leu Ser Ala Gly Tyr Gly Ile Asp Leu Asn Ser Tyr
        275                 280                 285

Leu Asn Glu Arg Gly Gln Ala Val Ala Ala Asp Thr Glu Asn His Cys
    290                 295                 300

Val Thr Asp Leu Pro Lys Ala Ala Phe Gln Gln Ser Ser Thr Leu Thr
305                 310                 315                 320

Arg Asp Gly Arg Gly Leu Leu Asp Tyr Leu Asp Glu Glu Pro Phe Ala
                325                 330                 335

Ser Val Ile Ala Asp Asn Arg Ile Gly Thr Ile Lys Pro Ser Val Pro
            340                 345                 350

Val Leu Ile Ser His Ser Val Ala Asp Asp Val Ile Pro Tyr Ala Val
        355                 360                 365

Gly Lys Gln Leu Ala Arg Asp Trp Cys Ala Lys Gly Ala Asn Val Arg
    370                 375                 380

Leu Ser Thr Asn Val Gly Pro Thr His Leu Gly Gly Ala Leu Pro Ser
385                 390                 395                 400
```

-continued

Ala Ala Glu Ser Tyr Ala Phe Phe Glu Ala Arg Phe Ala Gly Val Pro
405 410 415

Gln Leu Ser Asn Cys Trp Ala Val
420

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gaattcggga ccggactccg tgcccggcac 30

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
catatgacgt cagcactgct ccgacgagcc ctcgc 35

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aagcttctag acggcccagc agttgctgag 30

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gaattcgcac caccaccacc accacggacc ggactccgtg cccggcac 48

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
aagcttctag acggcccagc agttgctgag 30

<210> SEQ ID NO 35
<211> LENGTH: 396
<212> TYPE: PRT
<213> ORGANISM: Tetrasphaera sp.
<220> FEATURE:
<221> NAME/KEY: MOD_RES -continued

```
<222> LOCATION: (165)..(165)
<223> OTHER INFORMATION: Any amino acid

<400> SEQUENCE: 35

Gly Pro Asp Ser Val Pro Gly Thr Ala Gly Ala Thr Thr Val Thr Asp
1               5                   10                  15

Thr Pro Glu Pro Pro Arg Pro Ala Phe Tyr Glu Pro Pro Ala Thr Ile
            20                  25                  30

Pro Gly Thr Pro Gly Thr Val Ile Arg Thr Glu Ser Ala Thr Tyr Leu
        35                  40                  45

Leu Asp Pro Leu Gly Leu Ser Gln Thr Val Val Thr Ser Thr Arg Val
    50                  55                  60

Met Tyr Ser Ser Leu Asp Arg Gln Gly Arg Pro Ile Ala Val Thr Gly
65                  70                  75                  80

Thr Ile Leu Glu Pro Lys Ala Pro Trp Phe Gly Leu Gly Ala Arg Pro
                85                  90                  95

Leu Ile Ser Tyr Ala Val Gly Thr Gln Gly Met Gly Asp Arg Cys Ala
            100                 105                 110

Pro Ser Arg Gln Leu Ala Glu Ser Val Thr Glu Tyr Glu Ala Gly Phe
        115                 120                 125

Ile Ser Gly Leu Val Thr Arg Gly Tyr Ala Val Ala Phe Thr Asp Tyr
    130                 135                 140

Gln Gly Leu Ser Thr Pro Gly Thr His Thr Tyr Met Asn Arg Val Val
145                 150                 155                 160

Gln Gly Arg Ala Xaa Leu Asp Met Ala Arg Ala Ala Leu Arg Arg Asn
                165                 170                 175

Gly Thr Thr Leu Thr Ala Thr Thr Pro Val Gly Ile Tyr Gly Tyr Ser
            180                 185                 190

Gln Gly Gly Gly Ala Ser Ala Ser Ala Ala Glu Leu Thr Ala Thr Tyr
        195                 200                 205

Ala Pro Glu Leu Arg Val Lys Gly Ala Leu Ala Gly Ala Val Pro Ala
    210                 215                 220

Asp Leu Lys Ala Val Ala Gln Asn Leu Asp Gly Ser Leu Tyr Ala Glu
225                 230                 235                 240

Phe Leu Asn Phe Ala Leu Leu Gly Leu Ser Ala Gly Tyr Gly Ile Asp
                245                 250                 255

Leu Asn Ser Tyr Leu Asn Glu Arg Gly Gln Ala Val Ala Ala Asp Thr
            260                 265                 270

Glu Asn His Cys Val Thr Asp Leu Pro Lys Ala Ala Phe Gln Gln Ser
        275                 280                 285

Ser Thr Leu Thr Arg Asp Gly Arg Gly Leu Leu Asp Tyr Leu Asp Glu
    290                 295                 300

Glu Pro Phe Ala Ser Val Ile Ala Asp Asn Arg Ile Gly Thr Ile Lys
305                 310                 315                 320

Pro Ser Val Pro Val Leu Ile Ser His Ser Val Ala Asp Asp Val Ile
                325                 330                 335

Pro Tyr Ala Val Gly Lys Gln Leu Ala Arg Asp Trp Cys Ala Lys Gly
            340                 345                 350

Ala Asn Val Arg Leu Ser Thr Asn Val Gly Pro Thr His Leu Gly Gly
        355                 360                 365

Ala Leu Pro Ser Ala Ala Glu Ser Tyr Ala Phe Phe Glu Ala Arg Phe
    370                 375                 380

Ala Gly Val Pro Gln Leu Ser Asn Cys Trp Ala Val
385                 390                 395
```

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 36

His His His His His His
1 5

<210> SEQ ID NO 37
<211> LENGTH: 295
<212> TYPE: PRT
<213> ORGANISM: Streptomyces sp.

<400> SEQUENCE: 37

Met Pro Lys Pro Ala Leu Arg Arg Val Met Thr Ala Thr Val Ala Ala
1 5 10 15

Val Gly Thr Leu Ala Leu Gly Leu Thr Asp Ala Thr Ala His Ala Ala
20 25 30

Pro Ala Gln Ala Thr Pro Thr Leu Asp Tyr Val Ala Leu Gly Asp Ser
35 40 45

Tyr Ser Ala Gly Ser Gly Val Leu Pro Val Asp Pro Ala Asn Leu Leu
50 55 60

Cys Leu Arg Ser Thr Ala Asn Tyr Pro His Val Ile Ala Asp Thr Thr
65 70 75 80

Gly Ala Arg Leu Thr Asp Val Thr Cys Gly Ala Ala Gln Thr Ala Asp
85 90 95

Phe Thr Arg Ala Gln Tyr Pro Gly Val Ala Pro Gln Leu Asp Ala Leu
100 105 110

Gly Thr Gly Thr Asp Leu Val Thr Leu Thr Ile Gly Gly Asn Asp Asn
115 120 125

Ser Thr Phe Ile Asn Ala Ile Thr Ala Cys Gly Thr Ala Gly Val Leu
130 135 140

Ser Gly Gly Lys Gly Ser Pro Cys Lys Asp Arg His Gly Thr Ser Phe
145 150 155 160

Asp Asp Glu Ile Glu Ala Asn Thr Tyr Pro Ala Leu Lys Glu Ala Leu
165 170 175

Leu Gly Val Arg Ala Arg Ala Pro His Ala Arg Val Ala Ala Leu Gly
180 185 190

Tyr Pro Trp Ile Thr Pro Ala Thr Ala Asp Pro Ser Cys Phe Leu Lys
195 200 205

Leu Pro Leu Ala Ala Gly Asp Val Pro Tyr Leu Arg Ala Ile Gln Ala
210 215 220

His Leu Asn Asp Ala Val Arg Arg Ala Ala Glu Glu Thr Gly Ala Thr
225 230 235 240

Tyr Val Asp Phe Ser Gly Val Ser Asp Gly His Asp Ala Cys Glu Ala
245 250 255

Pro Gly Thr Arg Trp Ile Glu Pro Leu Leu Phe Gly His Ser Leu Val
260 265 270

Pro Val His Pro Asn Ala Leu Gly Glu Arg Arg Met Ala Glu His Thr
275 280 285

Met Asp Val Leu Gly Leu Asp
290 295

-continued

```
<210> SEQ ID NO 38
<211> LENGTH: 268
<212> TYPE: PRT
<213> ORGANISM: Streptomyces rimosus

<400> SEQUENCE: 38

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
        35                  40                  45

Val Gly Ala Gly Ser Tyr Asp Ser Ser Ser Gly Ser Cys Lys Arg Ser
    50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Val Leu Gly Tyr Pro
                165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Ala Asp Asp Ile Asn Ala Val Thr
        195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
            260                 265
```